(12) United States Patent
Yirme et al.

(10) Patent No.: US 8,501,474 B2
(45) Date of Patent: Aug. 6, 2013

(54) METHODS OF GENERATING EMBRYOID BODIES AND USES OF SAME

(75) Inventors: Galia Yirme, Kerem Maharal (IL); Joseph Itskovitz-Eldor, Haifa (IL)

(73) Assignee: Technion Research & Development Foundation Limited, Haifa (IL)

( * ) Notice: Subject to any disclaimer, the term of this patent is extended or adjusted under 35 U.S.C. 154(b) by 98 days.

(21) Appl. No.: 12/738,086

(22) PCT Filed: Oct. 5, 2008

(86) PCT No.: PCT/IL2008/001318
§ 371 (c)(1),
(2), (4) Date: Aug. 16, 2010

(87) PCT Pub. No.: WO2009/050694
PCT Pub. Date: Apr. 23, 2009

(65) Prior Publication Data
US 2010/0304486 A1    Dec. 2, 2010

Related U.S. Application Data

(60) Provisional application No. 60/960,783, filed on Oct. 15, 2007.

(51) Int. Cl.
*C12N 5/00*        (2006.01)
*C12N 5/02*        (2006.01)

(52) U.S. Cl.
USPC ............ 435/383; 435/375; 435/378; 435/381

(58) Field of Classification Search
None
See application file for complete search history.

(56) References Cited

U.S. PATENT DOCUMENTS

| | | | |
|---|---|---|---|
| 2004/0096967 | A1 | 5/2004 | Gryseels et al. |
| 2006/0134782 | A1 | 6/2006 | Gold et al. |
| 2006/0148078 | A1 | 7/2006 | Gerecht-Nir et al. |

FOREIGN PATENT DOCUMENTS

| | | |
|---|---|---|
| WO | WO 2004/039966 | 5/2004 |
| WO | WO 2009/050694 | 4/2009 |

OTHER PUBLICATIONS

Ng, Blood, 2005. 106:1601-1603.*
International Search Report Dated Mar. 4, 2009 From the International Searching Authority Re.: Application No. PCT/IL2008/001318.
Written Opinion Dated Mar. 4, 2009 From the International Searching Authority Re.: Application No. PCT/IL2008/001318.
Cameron et al "Improved Development of Human Embryonic Stem Cell-Derived Embryoid Bodies by Stired Vessel Cultivation", Biotechnology and Bioengineering, XP002515395, 94:(5) 938-948, Aug. 2006 Abstract.
Dang et al. "Efficiency of Embryoid Body Formation and Hemtopoietic Development From Embryonic Stem Cells in Different Culture Systems", Biotechnology and Bioengineering, 78: 442-453, 2002.
Gerecht-Nir et al. "Bioreactor Cultivation Enhances the Efficiency of Human Embryoid Body (hEB) Formation and Differentiation", Biotechnology and Bioengineering, XP002362425, 86(5): 493-502, Jun. 5, 2004. Abstract.
Kehat et al. "Human Embryonic Stem Cells Can Differentiate Into Myocytes With Structural and Functional Properties of Cardiomyocytes", The Journal of Clinical Investigation, 108: 407-414, 2001.
Kurosawa "Methods for Inducing Embryoid Body Formation: In Vitro Differentiation System of Embryonic Stem Cells", Journal of Bioscience and Bioengineering, XP022136677, 103(5): 389-398, May 1, 2007.
Schroeder et al. "Differentiation and Lineage Selection of Mouse Embryonic Stem Cells in a Stirred Bench Scale Bioreactor With Automated Process Control", Biotechnology and Bioengineering, XP002515393, 97(7): 920-933, Dec. 30, 2005. Abstract.
Xu et al. "Characterization and Enrichment of Cardiomyocytes Derived From Human Embryonic Stem Cells", Circulation Research, 91: 501-508, 2002.
Yamamoto et al. "Proliferation, Differentiation, and Tube Formation by Endiothelial Progenitor Cells in Response to Shear Stress", Journal of Applied Physiology, 95: 2081-2088, Jul. 11, 2003.
Yirme et al. Establishing a Dynamic Process for the Formation, Propagation, and Differentiation of Human Embryoid Bodies, Stem Cells and Development, XP009112308, 17(6): 1227-1241, Dec. 2008.
Zandstra et al. "Scalable Production of Embryonic Stem Cell-Derived Cardiomyocytes", Tissue Engineering, XP002515394, 9(4): 767-778, 2003.
International Preliminary Report on Patentability Dated Apr. 29, 2010 From the International Bureau of WIPO Re.: Application No. PCT/IL2008/001318.
Christi "Hydrodynamic Damage to Animal Cells", Critical Reviews in Biotechnology, 21(2): 67-110, 2001.
Dang et al. "Controlled, Scalable Embryonic Stem Cell Differentiation Culture", Stem Cells, 22: 275-282, 2004.
Livak et al. "Analysis of Relative Gene Expression Data Using Real-Time Quantitative PCR and the 2-??CT Method", Methods, 25(4): 402-408, Dec. 30, 2001.
Zweigerdt et al. "Generation of Confluent Cardiomyocyte Monolayers Derived From Embryonic Stem Cells in Suspension: A Cell Source for New Therapies and Screening Strategies", Cytotherapy, 5(5): 399-413, 2003.

* cited by examiner

*Primary Examiner* — Valarie Bertoglio

(57) ABSTRACT

Methods of generating embryoid bodies (EBs) by culturing embryonic stem cells (ESCs) under static conditions followed by culturing the cells under dynamic conditions using e.g., a Glass Bulb-shaped Impeller (GBI) or shaking a culture vessel are provided. Also provided are methods of generating expanded and/or differentiated cells from the EBs of the invention and methods of using same for treating disorders requiring cell replacement therapy.

15 Claims, 14 Drawing Sheets
(13 of 14 Drawing Sheet(s) Filed in Color)

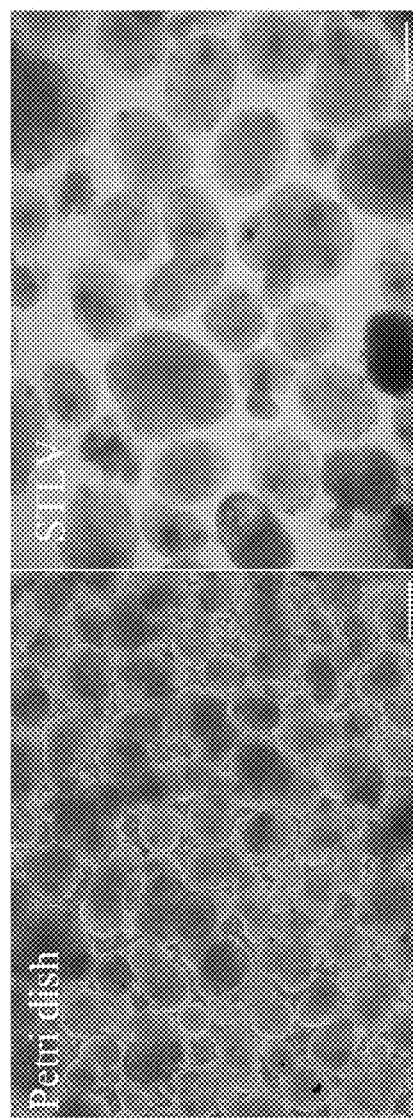
FIG. 1A
FIG. 1B
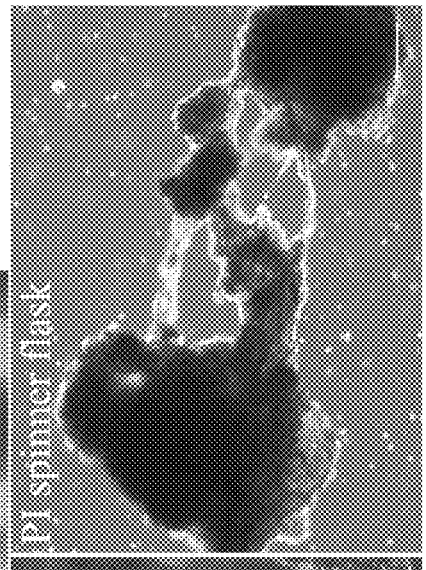
FIG. 1C
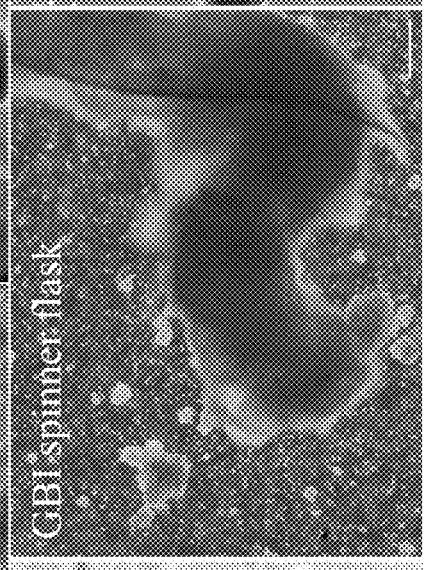
FIG. 1D
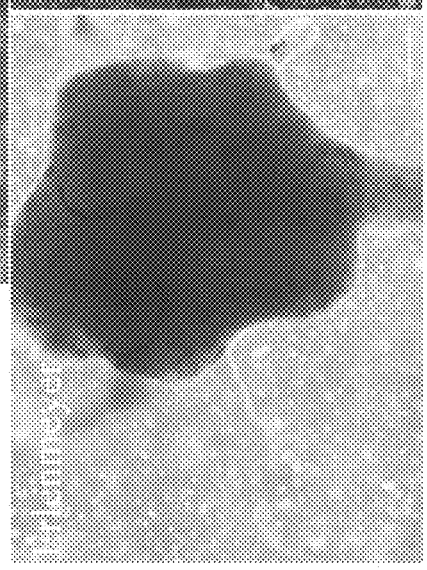
FIG. 1E

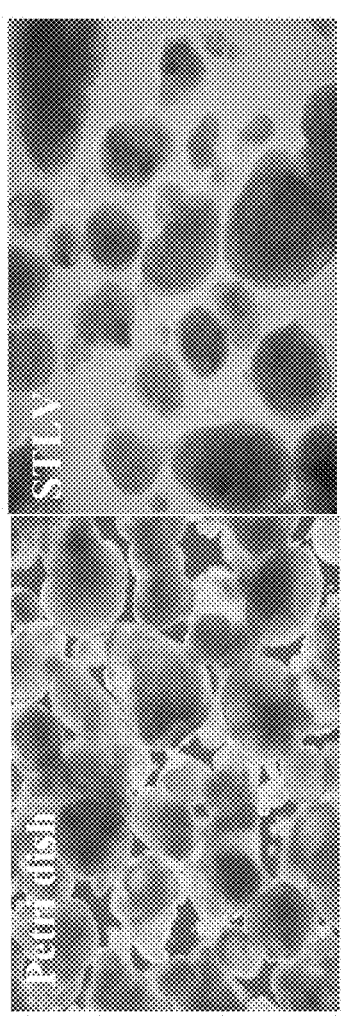
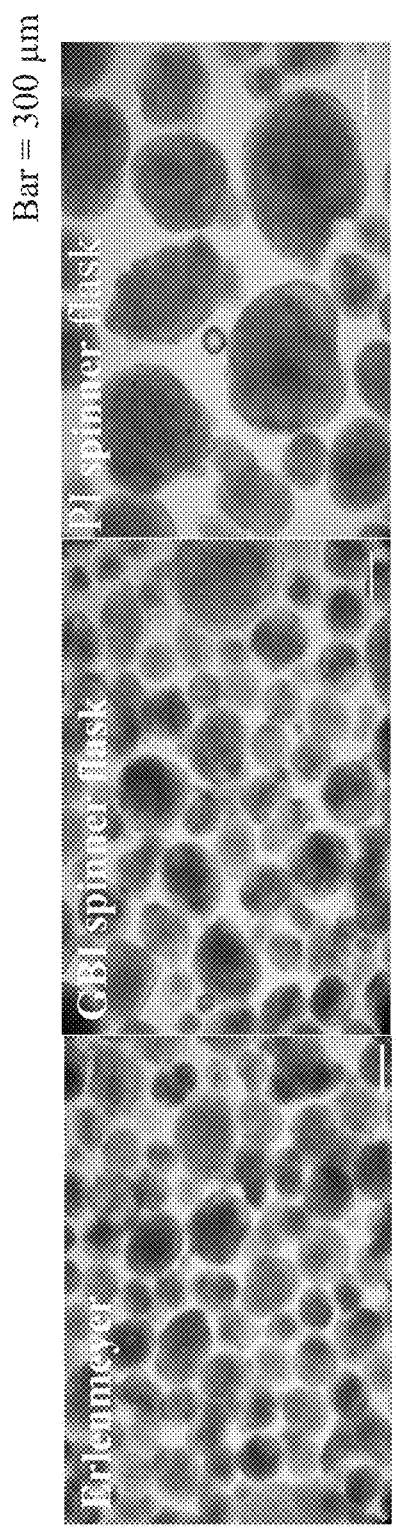
FIG. 2A  FIG. 2B  FIG. 2C  FIG. 2D  FIG. 2E

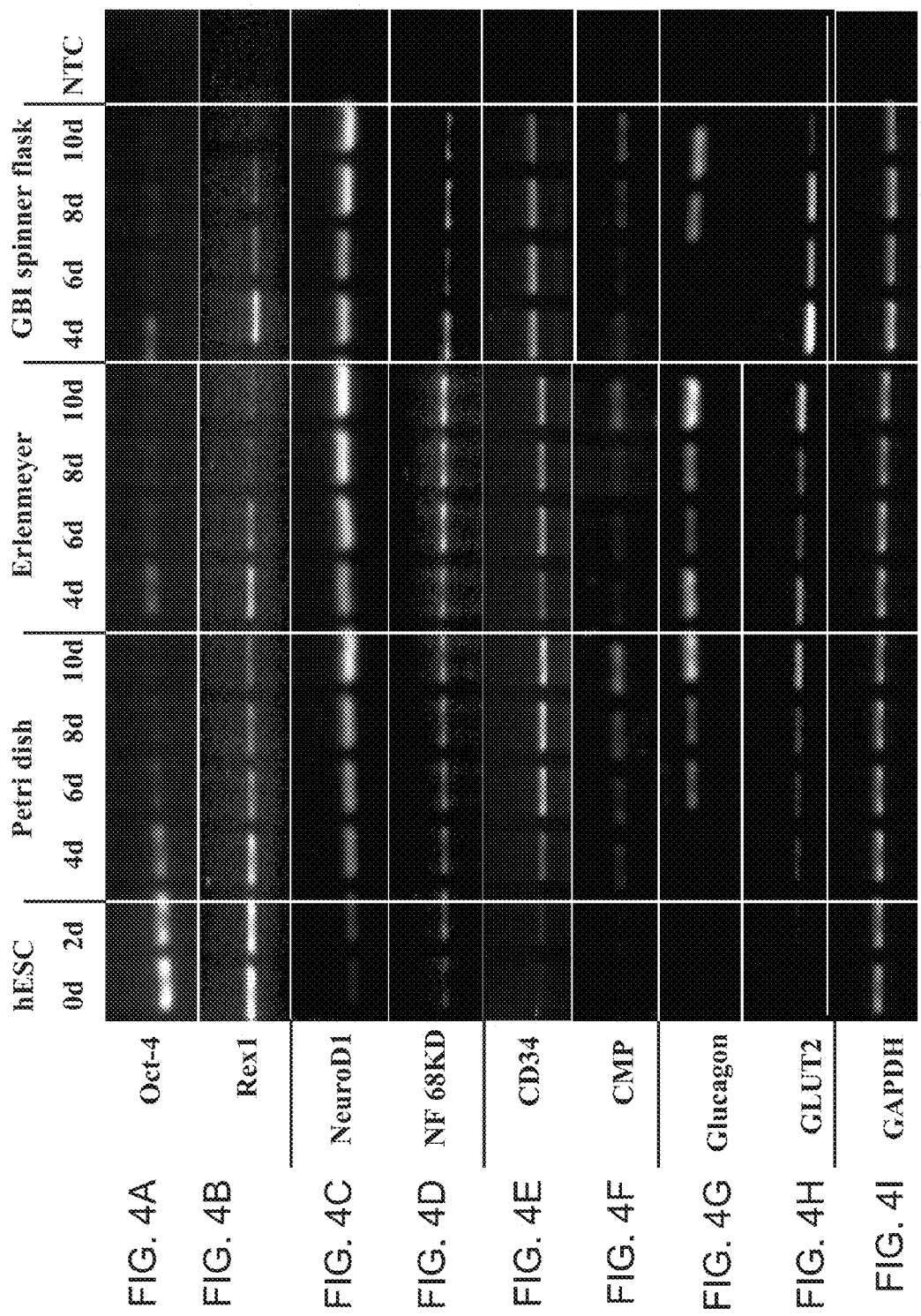

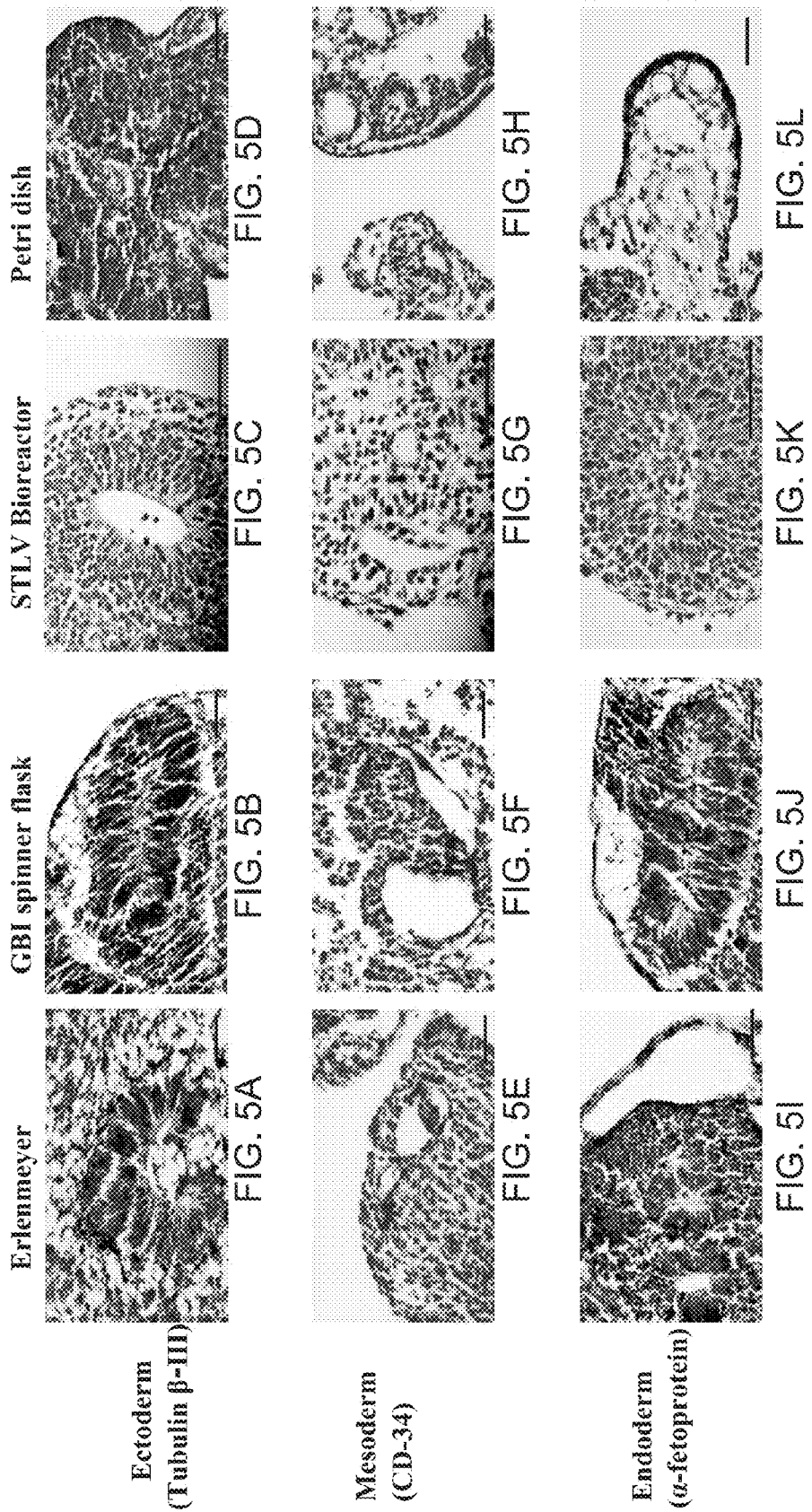

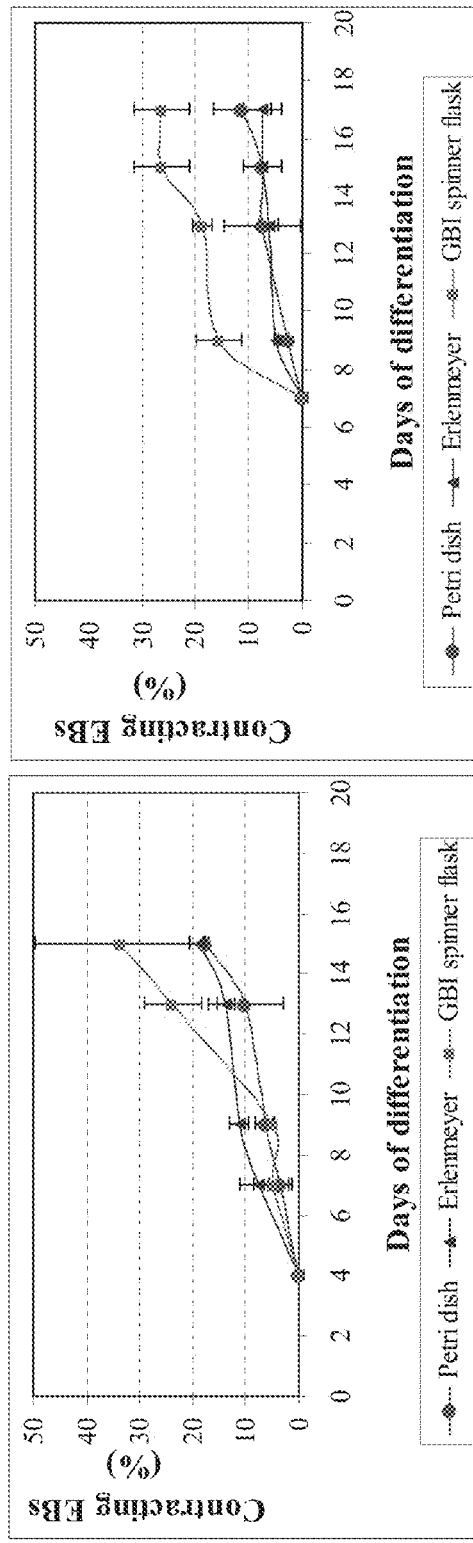
FIG. 6A
FIG. 6B
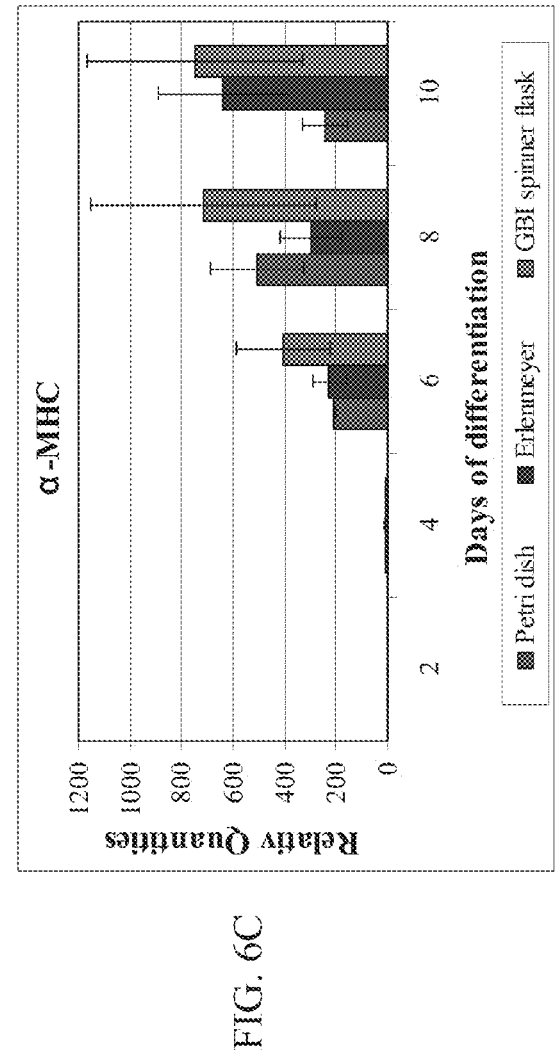
FIG. 6C

Petri dish

GBI spinner flask

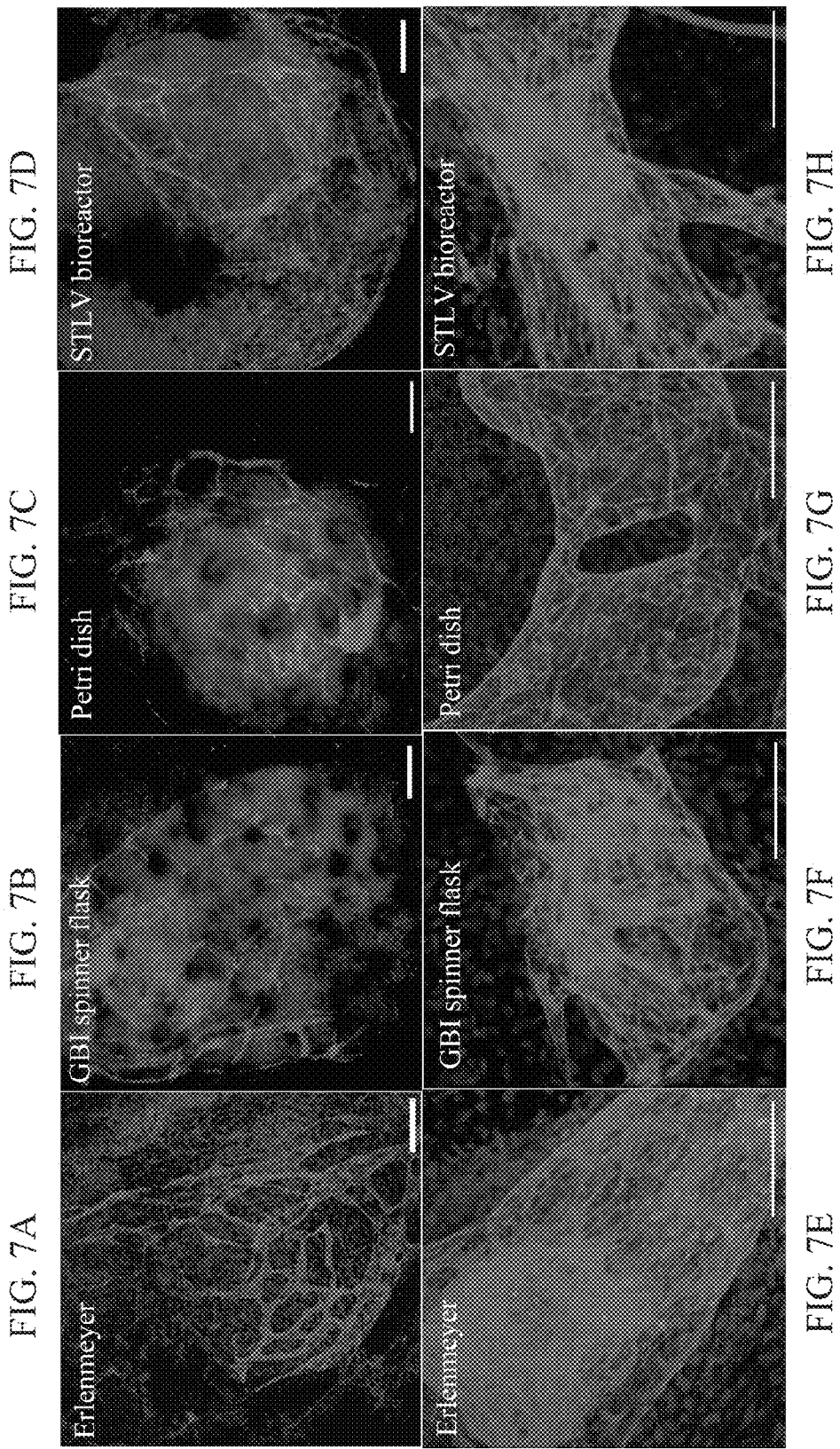

FIG. 8A
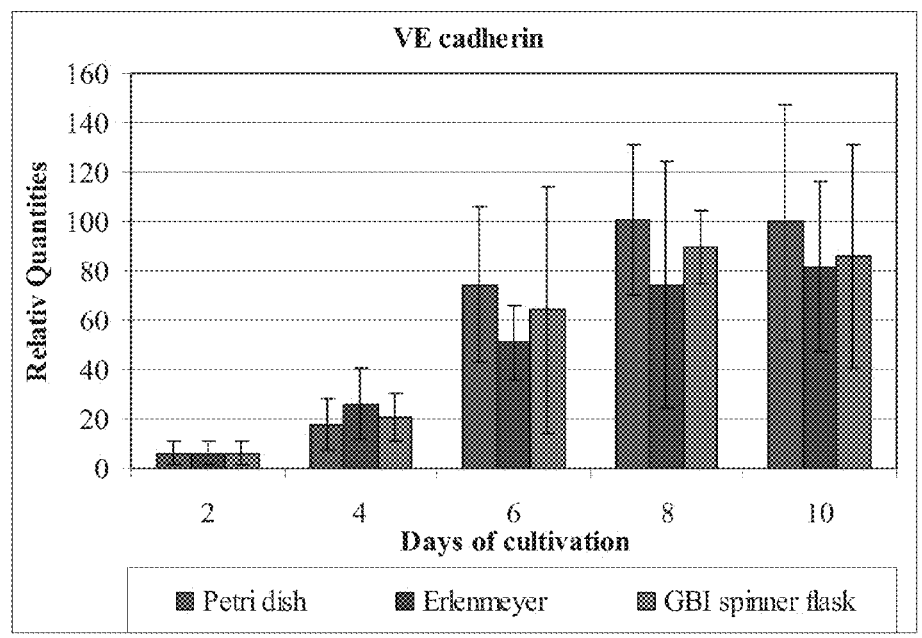
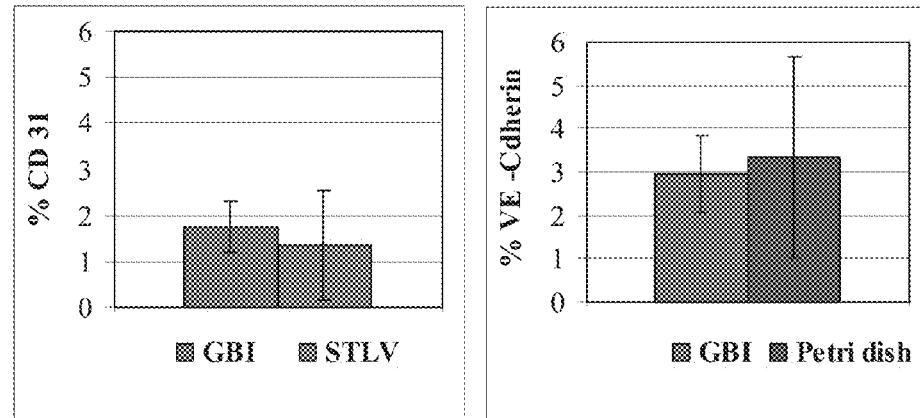
FIG. 8B               FIG. 8C

SEQUENCE LISTING

```
<160> NUMBER OF SEQ ID NOS: 16

<210> SEQ ID NO 1
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 1
gagaacaatg agaaccttca gga                                          23

<210> SEQ ID NO 2
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 2
ttctggcgcc ggttacagaa cca                                          23
```

<210> SEQ ID NO 3
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 3
gcgtacgcaa attaaagtcc aga                                          23

<210> SEQ ID NO 4
<211> LENGTH: 25
<212> TYPE: DNA
<213> ORGANISM: Artificial sequence
<220> FEATURE:
<223> OTHER INFORMATION: Single strand DNA oligonucleotide

<400> SEQUENCE: 4
cagcatccta aacagctcgc agaat                                        25

<210> SEQ ID NO 5
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 5
gagtgaaatg gcacgatacc ta                                           22

<210> SEQ ID NO 6
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 6
tttcctctcc ttcttcacct tc                                           22

<210> SEQ ID NO 7
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 7
cctcgaagcc atgaacgcag                                              20

<210> SEQ ID NO 8
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 8
gctgtccatg gtaccgtaag                                              20

<210> SEQ ID NO 9
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 9
acggctgact tcaagaccat                                              20

<210> SEQ ID NO 10
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 10
tcaataggca cacccagaca                                              20

<210> SEQ ID NO 11
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 11
caacacgtgg tggctgatac                                              20

<210> SEQ ID NO 12
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 12
tcaaagcttc ctgggagaaa                                              20

<210> SEQ ID NO 13
<211> LENGTH: 19
<212> TYPE: DNA
<213> ORGANISM: Artificial sequence
<220> FEATURE:
<223> OTHER INFORMATION: Single strand DNA oligonucleotide

<400> SEQUENCE: 13
aggcagaccc actcagtga                                               19

<210> SEQ ID NO 14
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 14
aacaatggcg acctcttctg                                              20

<210> SEQ ID NO 15
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 15
aggacttctg tggaccttat gtg                                          23

<210> SEQ ID NO 16
<211> LENGTH: 20
<212> TYPE: DNA
<213> ORGANISM: Artificial sequence

```
<220> FEATURE:
<223> OTHER INFORMATION: Single strand DNA oligonucleotide

<400> SEQUENCE: 16
gttcatgtca aaaagcaggg                                                    20
```

METHODS OF GENERATING EMBRYOID BODIES AND USES OF SAME

RELATED APPLICATIONS

This Application is a National Phase of PCT Patent Application No. PCT/IL2008/001318 having International filing date of Oct. 5, 2008, which claims the benefit of U.S. Provisional Patent Application No. 60/960,783 filed on Oct. 15, 2007. The contents of the above Applications are all incorporated herein by reference.

FIELD AND BACKGROUND OF THE INVENTION

The present invention, in some embodiments thereof, relates to methods of generating embryoid bodies and to cell cultures comprising same.

Human embryonic stem cells (hESCs) are pluripotent cells that can potentially differentiate into all cell types present in the adult body. However, the promise of hESCs in providing unlimited supply of cells for therapy greatly depends on the availability of controllable large-scale bioprocesses. Potential industrial applications will require a large number of cells, thus enhancing the need to develop scalable methods for the production and differentiation of hESCs. The culture volumes of few milliliters utilized in basic biology must be adapted to clinically relevant scales of up to hundreds of liters.

In-vitro ESCs differentiation commonly requires spontaneous formation in suspension of spherical cell clusters called embryoid bodies (EBs). Typically, EBs include cells derivatives of all three primary germ layers—endoderm, mesoderm and ectoderm. It is known that mouse EBs can be generated from a single mouse ESC. In contrast, due to the low clonality of human ESCs, formation of human EBs requires initial ESCs aggregation while preventing EBs' agglomeration, which may affect cell proliferation and differentiation and cause extensive cell death (Dang S M., et al., 2002; Schroeder M., et al., 2005; Xu et al., 2002; Dang et al., 2004). Standard methods of generating EBs include hanging drop, liquid suspension and methylcellulose culture. However, these methods are not efficient for the industrial arena due to their complexity.

Direct seeding of mESCs into a spinner flask equipped with a paddle-impeller resulted in the formation of large ESC clumping and agglomeration within 3 days (Schroeder M., et al., 2005). Attempts to avoid agglomeration include increase of stirring rate (Chisti, 2001); encapsulation of mESCs prior to seeding in the stirred culture (U.S. Pat. Appl. No. 20030119107 to Dang and Zandstra); pre-incubation of mouse EBs in Petri dishes prior to their transfer into paddle impeller spinner flasks (Zandstra et al., 2003); spinning of Petri dishes on a horizontal rotation device (Zweigerdt et al., 2003); direct seeding of mESCs into spinner flasks equipped with a glass bulb-shaped impeller or into a 2-liter vessel equipped with a pitched-blade turbine impeller (Schroeder et al., 2005) or direct seeding of mESCs into Fernbach flask on a rotary shaker (WO 04039966 to Gryseels T D et al.).

Cameron C M., et al., 2006, describe formation of hEBs by cultivation of human ESCs in a spinner flask which contains a magnetic stir bar.

U.S. Pat. Appl. No. 20060148078 and Gerecht-Nir et al. 2004 describe dynamic generation of human embryoid bodies in bioreactors such as the Rotating Wall Vessel (RWV) bioreactor (known also as Slow Turning Lateral Vessel—STLV).

Additional background art includes Wartenberg et al., 1998; U.S. Pat. Appl. No. 20040096967; U.S. Pat. Appl. No. 20060134782.

SUMMARY OF THE INVENTION

According to an aspect of some embodiments of the present invention there is provided a method of generating embryoid bodies, comprising: (a) culturing embryonic stem cells under static conditions; and subsequently (b) culturing the embryonic stem cells under dynamic conditions using a Glass Bulb-shaped Impeller (GBI); thereby generating the embryoid bodies.

According to an aspect of some embodiments of the present invention there is provided a method of generating embryoid bodies, comprising: (a) culturing embryonic stem cells under static conditions; and subsequently (b) culturing the embryonic stem cells under dynamic conditions which comprise shaking a culture vessel comprising the embryonic stem cells; thereby generating the embryoid bodies. According to an aspect of some embodiments of the present invention there is provided a method of generating embryoid bodies, comprising: (a) culturing embryonic stem cells under static conditions; and subsequently (b) culturing the embryonic stem cells under dynamic conditions so as to obtain at least 5 fold expansion following six days of the culturing under the dynamic conditions; thereby generating the embryoid bodies. According to an aspect of some embodiments of the present invention there is provided a method of generating embryoid bodies, comprising: (a) culturing embryonic stem cells under static conditions; and subsequently (b) culturing the embryonic stem cells under dynamic conditions so as to obtain embryoid bodies which include no more than 4% of apoptotic cells following 10 days in culture; thereby generating the embryoid bodies.

According to an aspect of some embodiments of the present invention there is provided a cell culture comprising embryoid bodies, wherein an average diameter of the embryoid bodies does not exceed about 400 µm.

According to an aspect of some embodiments of the present invention there is provided a cell culture comprising embryoid bodies generated according to the method of the invention.

According to an aspect of some embodiments of the present invention there is provided a method of generating expanded and/or differentiated cells from embryonic stem cells comprising: (a) culturing embryonic stem cells according to the method of the invention, to thereby generate embryoid bodies; (b) isolating lineage specific cells from the embryoid bodies, and; (c) culturing the lineage specific cells under culturing conditions selected suitable for the expansion and/or differentiation of the lineage specific cells to thereby obtain the expanded and/or differentiated lineage-specific cells.

According to an aspect of some embodiments of the present invention there is provided a method of generating expanded and/or differentiated cells from embryonic stem cells comprising: (a) isolating lineage specific cells from the embryoid bodies of the cell culture of the invention, and; (b) culturing the lineage specific cells under culturing conditions selected suitable for the expansion and/or differentiation of the lineage specific cells to thereby obtain the expanded and/or differentiated lineage-specific cells.

According to an aspect of some embodiments of the present invention there is provided a method of treating a disorder requiring cell replacement therapy comprising: (a) generating expanded and/or differentiated cells from embryonic stem cells according to the method of the invention, and;

(b) administering cells of the expanded and/or differentiated lineage-specific cells to an individual in need thereof thereby treating the disorder requiring the cell replacement therapy.

According to some embodiments of the invention, culturing in step (a) is effected for about 2 days.

According to some embodiments of the invention, the static conditions comprise culturing the embryonic stem cells in a Rotating Wall Vessel (RWV) bioreactor.

According to some embodiments of the invention, the dynamic conditions enable a growth rate of at least 1.6 day$^{-1}$.

According to some embodiments of the invention, the dynamic conditions enable at least 5 fold expansion of the embryonic stem cells following six days of the culturing under the dynamic conditions.

According to some embodiments of the invention, the dynamic conditions are selected suitable for generating embryoid bodies which include no more than 4% of apoptotic cells following 10 days in culture.

According to some embodiments of the invention, the embryoid bodies are devoid of necrotic centers.

According to some embodiments of the invention, an average diameter of the embryoid bodies does not exceed about 400 μm.

According to some embodiments of the invention, the dynamic conditions comprise exposing the cells to lower shear forces as compared to shear forces generated when stirring the cells with a paddle impeller.

According to some embodiments of the invention, the dynamic conditions comprise stirring said GBI at a rate of about 75 rounds per minute.

According to some embodiments of the invention, the culture vessel is an Erlenmeyer.

According to some embodiments of the invention, the culturing in step (a) is effected by seeding initiation nucleus foci (INF) which comprise about 1300-1600 of the embryonic stem cells.

According to some embodiments of the invention, the culturing in step (a) is effected by seeding the embryonic stem cells at an initial concentration of about 0.3-1×10$^6$ cells per milliliter medium.

According to some embodiments of the invention, the cells comprised in the embryoid bodies exhibit normal karyotype.

According to some embodiments of the invention, the culturing of the embryonic stem cells is effected in a culture medium selected suitable for embryoid bodies formation.

According to some embodiments of the invention, the culture medium comprises 80% KO-DMEM, 20% serum, 1% Penicillin-Streptomycin, 1 mM L-glutamine, and 1% non-essential amino acid stock.

According to some embodiments of the invention, the embryoid bodies differentiate into cardiomyocytes.

According to some embodiments of the invention, the embryoid bodies spontaneously contract when transferred to gelatin-coated plates.

According to some embodiments of the invention, the embryonic stem cells are human embryonic stem cells.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

Figure 1F:
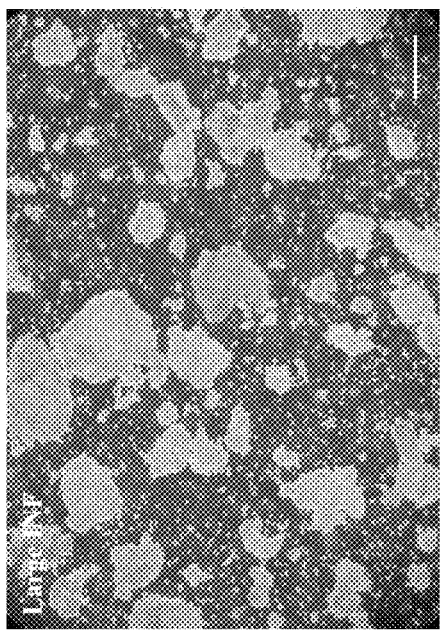

FIGS. 1A-E are microscopic images depicting the effect of shear forces at the time of seeding human embryonic stem cells (hESCs) in a culture medium on the formation of human embryoid bodies (hEBs). Human ESCs were seeded directly into stirred, static Petri dish or STLV systems and presence of EBs was monitored. Shown are phase contrast images of 2 day-old EBs seeded directly into the different culture systems. FIG. 1A—Petri dish (under static conditions); FIG. 1B—STLV; FIG. 1C—Erlenmeyer; FIG. 1D-GBI spinner flask; FIG. 1E-PI spinner flask. Note that direct seeding of hESCs into stirred systems (FIGS. 1C-F) resulted in extensive EBs aggregation and low EBs concentration after 2-days of cultivation. In contrast, direct seeding into the RWV bioreactor (FIG. 1B) or static Petri-dishes (FIG. 1A) had no such effect, probably due to the absence of shear forces. Scale bar—300 μm.

Figure 1G:
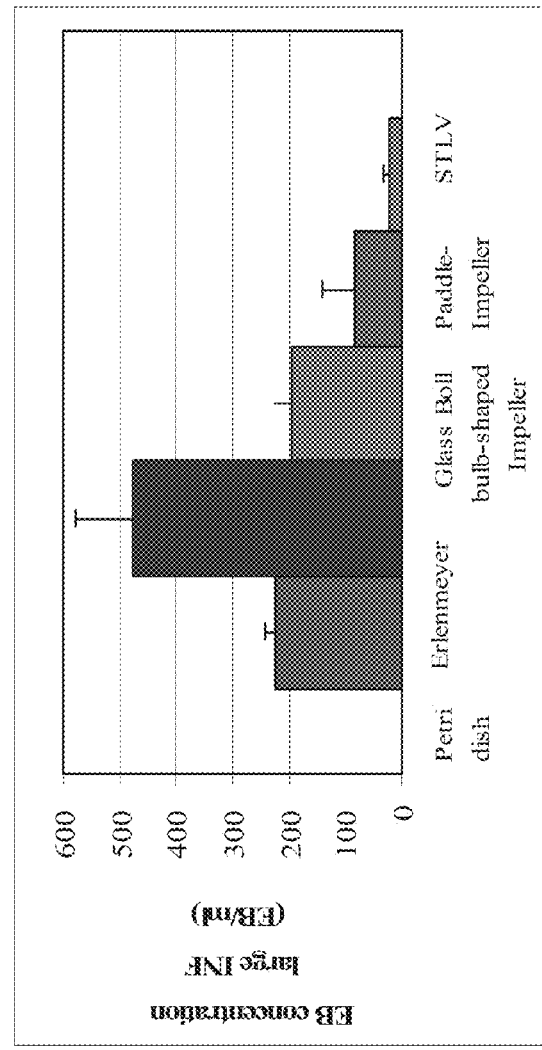
Figure 1H:
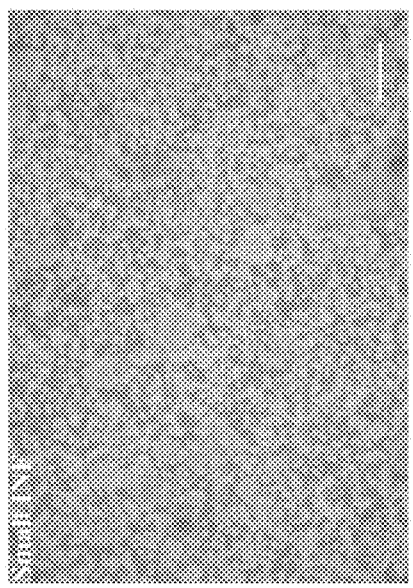
Figure 1I:
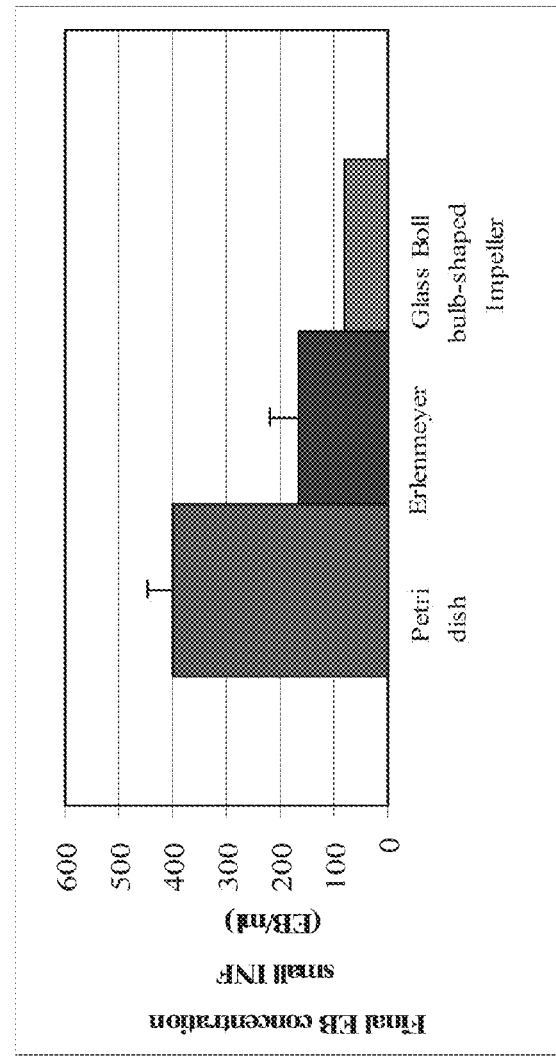

FIGS. 1F-I are microscopic images (FIGS. 1F and 1H) and histograms (FIGS. 1G and 1I) depicting the effect of initiation nucleus foci (INF) size on the final concentration of 10 day-old EBs. Human ESCs were seeded at a concentration of 0.7±0.1×10$^6$ viable hESCs/ml in static culture systems (Petri dishes) and following 2 days the cultured cells (2-day old EBs) were transferred to the stirred, static Petri dish or STLV culture systems. The initiation nucleus foci size of the hESCs at the time of the initial seeding in the static culture system was established by the mechanical breakdown of the cells: large INF were established by gentle mechanical breakdown with a pipette 300 μm in diameter; and small INF were established by intensive mechanical breakdown with a pipette 100 μm in diameter. FIG. 1F—phase contrast image of large INF. Scale bar=300 μm; FIG. 1G—a histogram depicting the concentration of 10-day old hEBs (EBs/ml) obtained from initial seeding of large INF in static culture system (for 2 days) followed by culturing in the following culturing systems: static culture (Petri dish; red), shaking Erlenmeyer (blue), Glass Bulb-shaped Impeller (GBI, green), Paddle-Impeller (PI, purple), or STLV (orange). FIG. 1H—phase contrast image of small INF. Scale bar=300 μm; FIG. 1I—a histogram depicting the concentration of 10-day old hEBs (EBs/ml) obtained from initial seeding of small INF in static culture system (for 2 days) followed by culturing in the following culturing systems: static culture (Petri dish; red), shaking Erlenmeyer (blue), Glass Bulb-shaped Impeller (GBI, green). The results shown were obtained from two different experiments performed in duplicate.

FIGS. 2A-F are microscopic images (FIGS. 2A-E) and a histogram (FIG. 2F) depicting hEB size distribution in stirred systems vs. STLV and static systems. Culture systems seeded with large INF and at a concentration of 0.7±0.1×10$^6$ viable ESCs/ml. EBs seeded into the stirred systems were first allowed 2 days of EB formation in the static Petri dish prior to seeding in the stirred or STLV culture systems. FIGS. 2A-E—

Figure 2F:
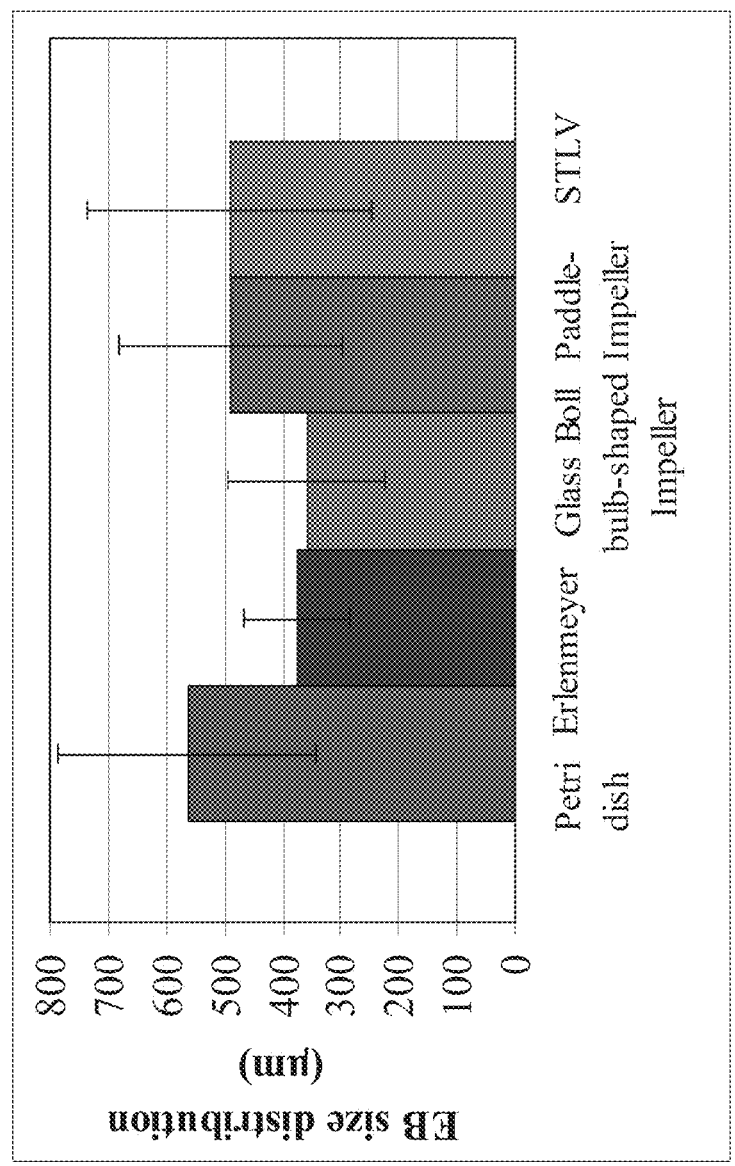

Light microscopy analyses of 10 day-old EBs in the static Petri-dish (FIG. 2A), STLV bioreactor (FIG. 2B), shaking Erlenmeyer (FIG. 2C), and stirred GBI (FIG. 2D) and PI spinner (FIG. 2E) flasks. Scale bar—300 µm. Note the relatively homogenous, small and round EBs established in the Erlenmeyer (FIG. 2C) and GBI (FIG. 2D) spinner flasks as compared with the larger and less homogenous EBs established in the other systems (FIGS. 2A, B and E). FIG. 2F—A histogram depicting size distribution of 10 day-old EBs in the following culture systems: Static (Petri dish, red), shaking Erlenmeyer (blue), GBI (green), PI (purple) and STLV (orange). The results shown are mean values [±standard deviation (SD)] of samples obtained from two different experiments performed in duplicate. Note the relatively small and homogenous EBs established in the Erlenmeyer (blue bar; average diameter 375±93 µm) and GBI spinner flask (green bar; average diameter 358±135 µm).

Figure 3A:
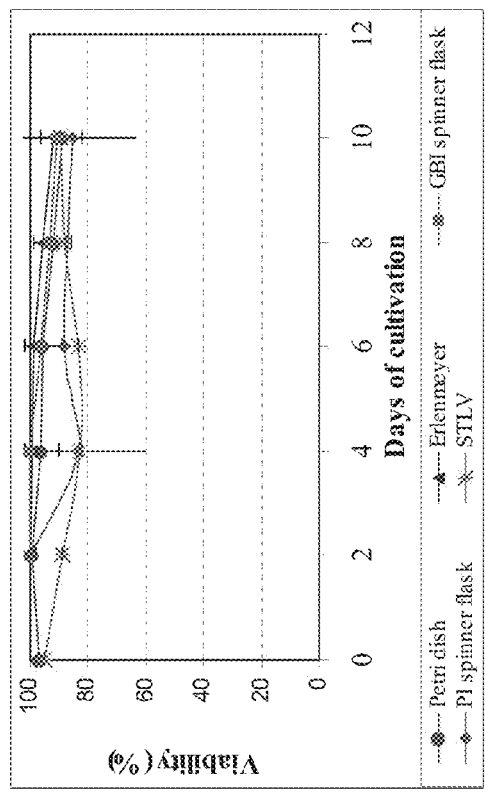
Figure 3B:
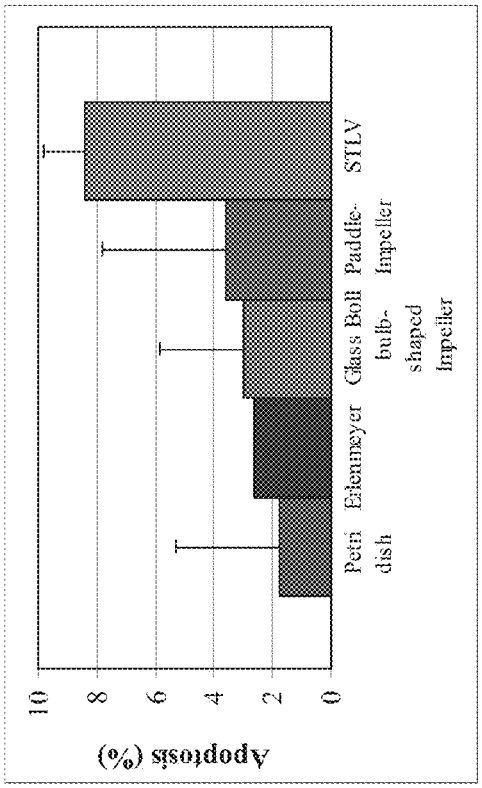
Figure 3C:
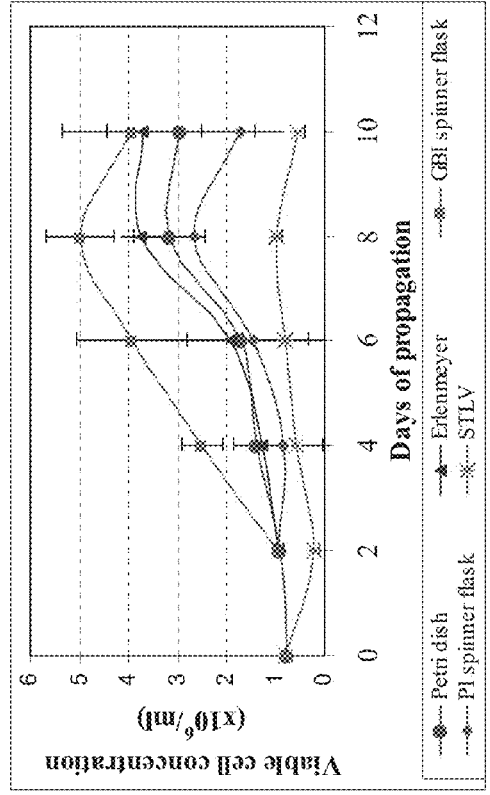
Figure 3D:
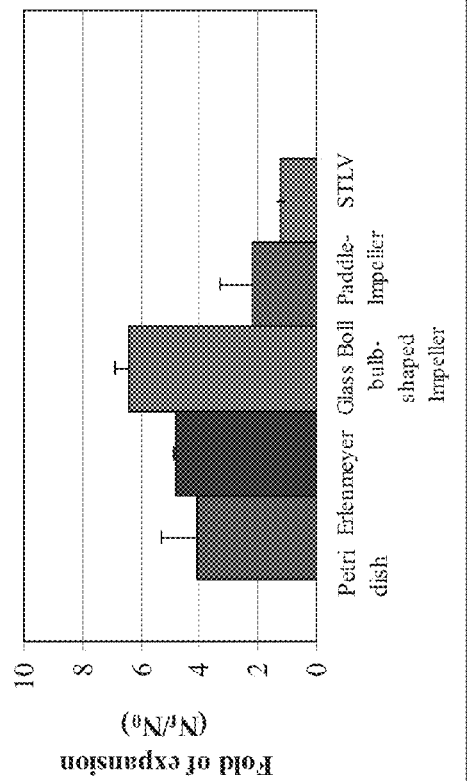

FIGS. 3A-D are graphs (FIGS. 3A and 3C) and histograms (FIG. 3B and FIG. 3D) depicting growth kinetics, viability and apoptosis in stirred systems vs. STLV and static systems. Culture systems were seeded with large INF; $0.7\pm0.1\times10^6$ viable ESCs/ml. EBs seeded into the stirred systems were first allowed 2 days of EB formation in the static Petri dish prior to seeding in the following culture systems: Static (Petri dish, red), shaking Erlenmeyer (blue), GBI (green), PI (purple) and STLV (orange). FIG. 3A—Kinetics of viable EBs' cell concentration during culturing period; FIG. 3B—Folds of expansion of hEBs; FIG. 3C—Viability during 10 cultivation days; FIG. 3D—Survival potential by apoptosis percentage in 10 day-old EBs at the end of cultivation. The results shown are mean values (±SD) of samples obtained from two different experiments performed in duplicate. Note that the GBI spinner flasks show the longest accelerate growth phase, without lag or stationary growth phases, which lead to highest viable cell concentration and highest fold of expansion.

Figure 3I:
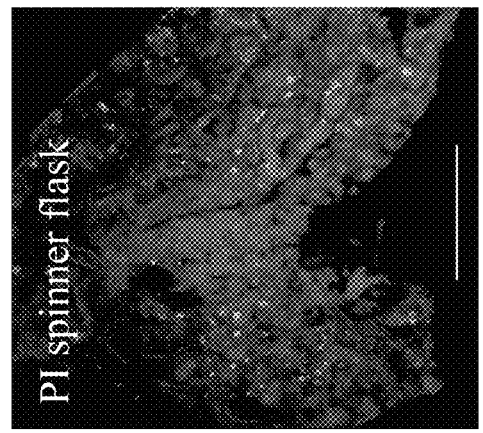
Figure 3F:
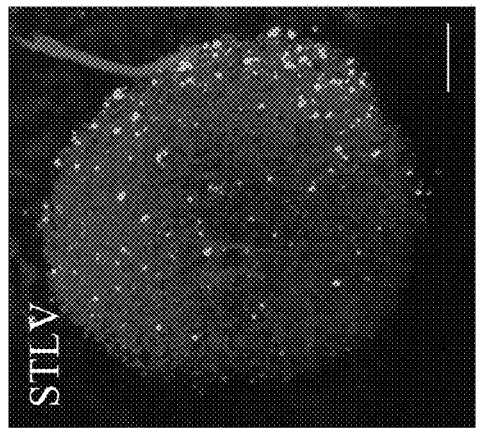
Figure 3H:
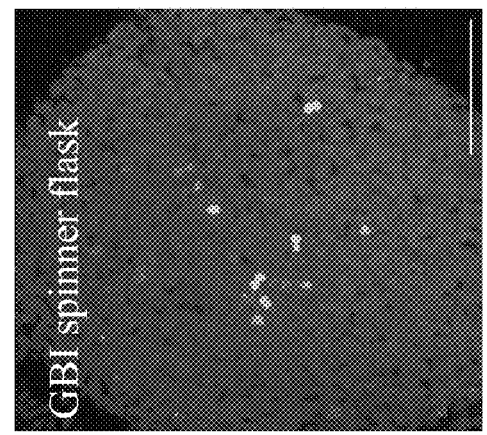
Figure 3E:
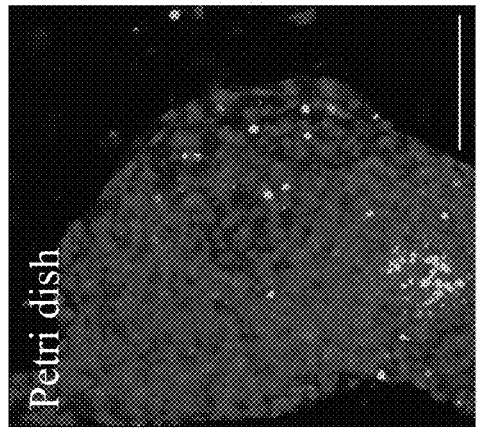
Figure 3G:
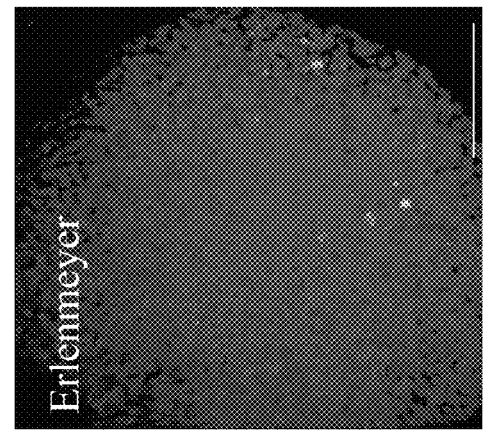

FIGS. 3E-I are microscopic images depicting location of apoptosis in whole EBs at day 10 of culturing. EBs were generated as described hereinabove with respect to FIGS. 3A-D and apoptosis locations in whole EBs was analyzed by immunofluorescence of entire EBs and visualized by confocal microscopy. FIG. 3E—EBs cultured in static culture system (Petri dish); FIG. 3F—EBs cultured in STLV; FIG. 3G—EBs cultured in shaking Erlenmeyer; FIG. 3H—EBs cultured in GBI spinner flask; FIG. 3I—EBs cultured in PI spinner flask; Scale bar=100 µm. Note that both viability and survivability remained high at the Erlenmeyer (FIG. 3G) and GBI spinner flask (FIG. 3H) during the entire cultivation period, while the STLV presented high apoptosis.

FIGS. 4A-I are RT-PCR analyses depicting differentiation potential of hEBs in stirred systems vs. STLV and static systems. RT-PCR analyses were performed on RNA samples of EBs cultured at static and stirred systems using gene-specific primers as described under "General Materials and Experimental Methods" in the Examples section which follows. FIG. 4A—Oct-4; FIG. 4B—Rex1; FIG. 4C—NeuroD1; FIG. 4D—NF 68 KD; FIG. 4E—CD34; FIG. 4F—CMP; FIG. 4G—Glucagon; FIG. 4H—GLUT2; FIG. 4I—GAPDH; Note the expression of genes of the three germ layers in both the Erlenmeyer and the GBI spinner flask versus the static conventional system, during cultivation, along with the vanishing of the undifferentiated genes. No significant differences were observed in the pattern of gene expression between the stirred, the STLV and the static culture. No template (NTC) reaction for each gene is shown on the right.

FIGS. 5A-L are microscopic images depicting immunostaining of tissues derived from the three germ layers in the differentiating 10 day-old EBs. hEBs formed in shaking Erlenmeyer (FIGS. 5A, E and I), GBI (FIGS. 5B, F and J), STLV (FIGS. 5C, G and K) and static Petri dish (FIGS. 5D, H and L). Staining was performed with antibodies specific to Tubulin β-III (FIGS. 5A-D), CD34 (FIGS. 5E-H) and α-fetoprotein (FIGS. 5I-L). Note the primitive neuronal tubes positive for β-tubulin III (ectodermal marker), blood vessels stained with anti-CD34 (mesodermal marker) and α-fetoprotein production (endodermal marker). Scale bar=50 µm.

FIGS. 6A-C are graphs (FIGS. 6A and 6B) and a histogram (FIG. 6C) depicting cardiac differentiation potential of hEBs under shear force conditions of stirred systems. hEBs cultured for 4 or 7 days in the stirred or static culture systems (in all cases initial culturing included 2 days in the static culture system prior to transfer to the stirred culture system), following which the EBs were transferred to gelatin-coated plates to allow further differentiation into spontaneous contracting cardiomyocytes. FIGS. 6A-B—Percentage of contracting EBs during differentiation on gelatin-coated plates after culturing for 4 (FIG. 6A) or 7 (FIG. 6B) days in suspension in Petri dish under static conditions (red), shaking Erlenmeyer (blue) or GBI (green) culture systems. FIG. 6C-R*eal* time RT-PCR of cardiac-specific α-MHC transcripts during cultivation; Note the clear correlation between the high quantity of α-MHC and the high percentage of contracting EBs in the GBI spinner flask.

Figure 6D:
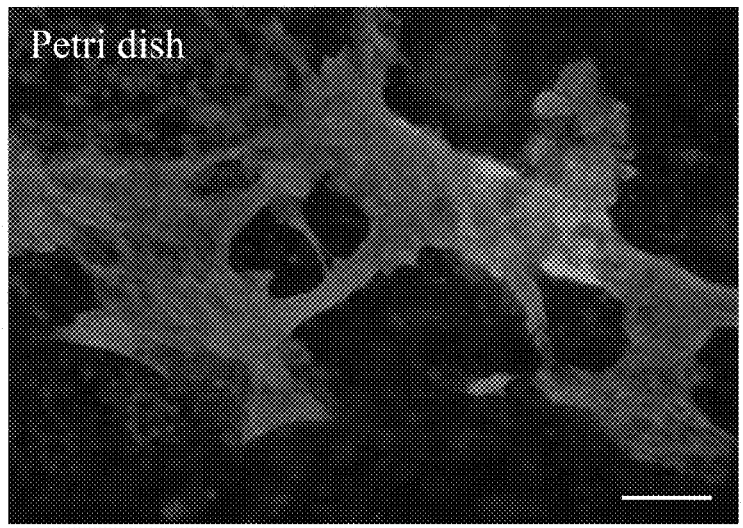
Figure 6E:
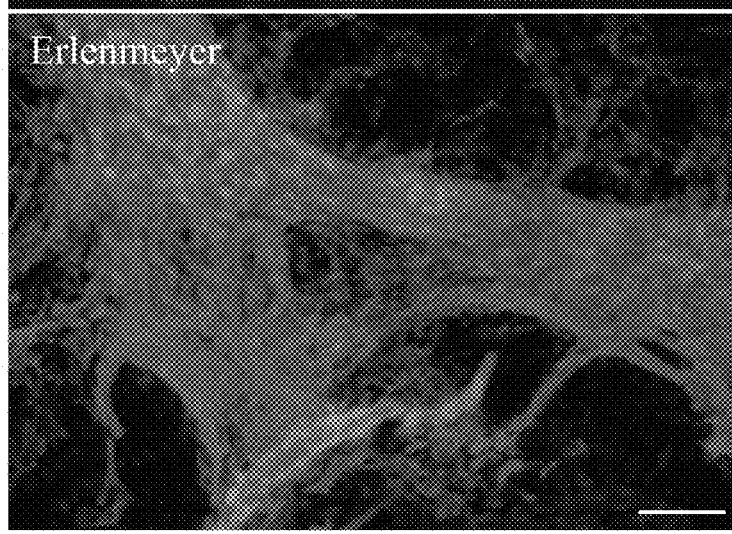
Figure 6F:
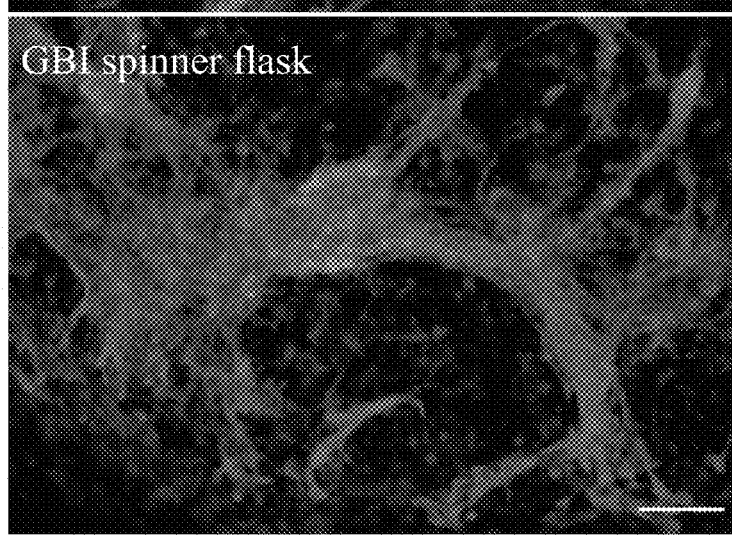

FIGS. 6D-F are microscopic images depicting fluorescence staining of contracting EBs (17 days-old) which were positive for cardiac-specific troponin I (cTnI). Scale bar=100 µm.

Figure 6G:
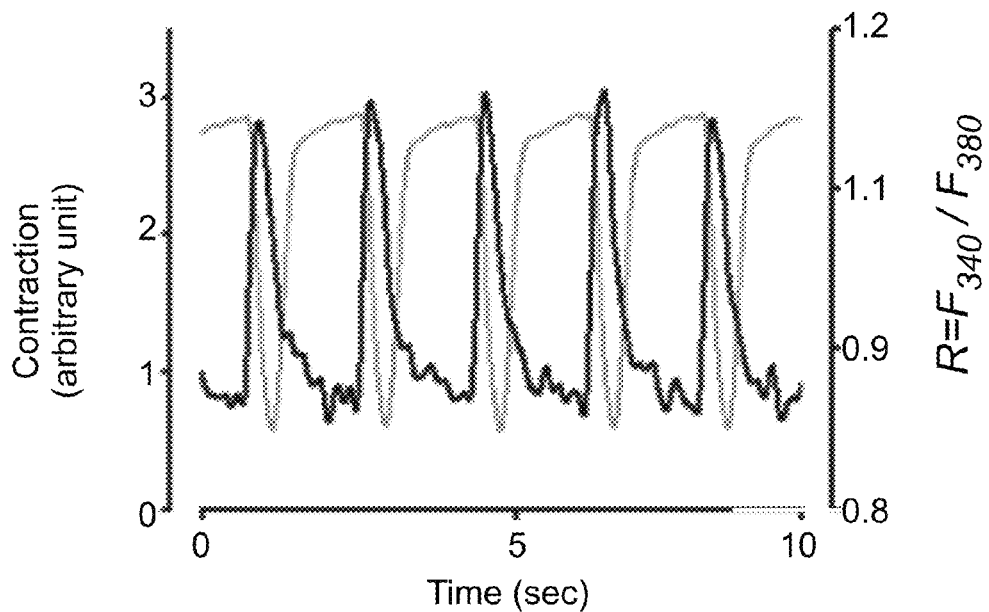
Figure 6H:
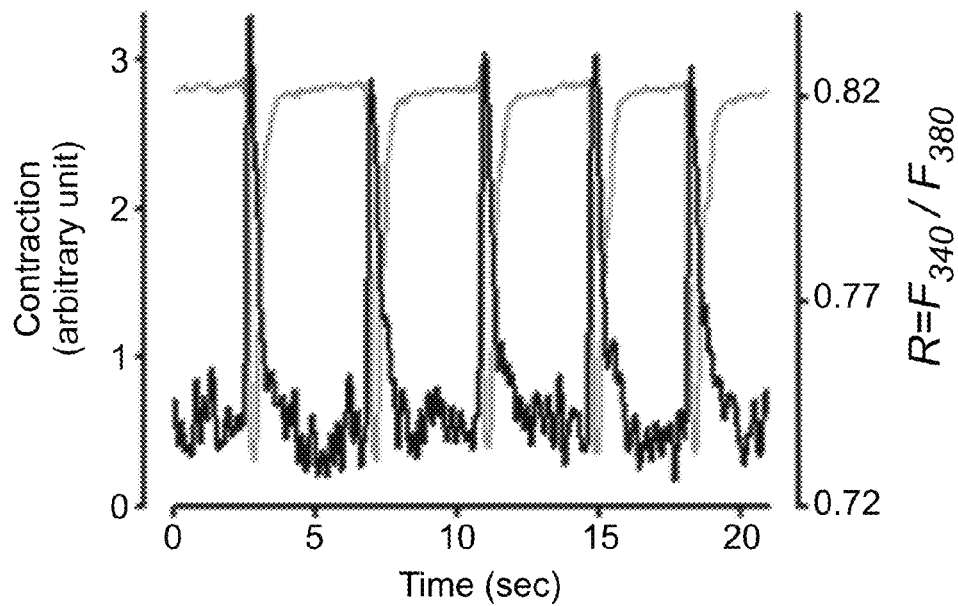

FIGS. 6G-H are graphs depicting functional properties of hESC-derived cardiomyocytes displayed by temporally related $[Ca^{2+}]I$.

FIGS. 7A-H are confocal microscopic images depicting 12 day-old hEBs stained for CD31. FIG. 6A—Erlenmeyer; FIG. 6B—GBI; FIG. 6C—Petri dish; FIG. 6D—STLV bioreactor; FIG. 6E—Erlenmeyer; FIG. 6F—GBI; FIG. 6G—Petri dish; FIG. 6H—STLV bioreactor. Note the three-dimensional network formation, vascular-like channels at the Erlenmeyer (FIGS. 7A and E) and the GBI spinner flask (FIGS. 7B and F) as compared to the culture system that did not induce shear forces [i.e., STLV (FIGS. 7D and H) and the static Petri dish (FIGS. 7C and F)]. Magnifications: FIGS. 7A-D—×17 Objective; FIGS. 7E-H—×40 Objective. Scale bars=100 µm.

FIGS. 8A-C are histograms depicting RT-PCR (FIG. 8A) and FACS (FIGS. 8B and C) analyses of hEBs cultivated in the static or stirred culture systems. FIG. 8A—a histogram depicting the results of real-time RT-PCR analysis of VE-cadherin of hEBs cultured in Petri dish (red), Erlenmeyer (blue) and GBI spinner flask (green). FIGS. 8B-C are histograms depicting the results of CD31 (FIG. 8B) or VE-Cadherin (FIG. 8C) FACS analyses performed on hEBS cultivated in GBI (green), STLV (orange) or Petri dish (red) culture systems. The results demonstrate the endothelial differentiation potential of hEBs under shear force conditions of stirred systems. Note that no obvious difference was detected between the 4 culture systems.

DESCRIPTION OF SPECIFIC EMBODIMENTS OF THE INVENTION

The present invention, in some embodiments thereof, relates to methods of generating embryoid bodies and using same for generating lineage specific cells which can be used in therapeutic applications.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

While reducing the present invention to practice, the present inventors have uncovered a novel method for large-scale generation of human embryoid bodies which may be used in a myriad of research and clinical applications.

Thus, as shown in the Examples section which follows, the human embryoid bodies (EBs) generated according to the novel method of the invention exhibit a logarithmic growth phase up to day 8 of cultivation followed by stationary phase (FIG. 3A; Example 3), with a high cell viability (e.g., 3.7-5.0×10$^6$ cells/ml on day 8 of culture; FIG. 3A), a fast growth rate (e.g., 1.9 day$^{-1}$-2.3 day$^{-1}$), and a high fold expansion (4.8-6.4 during 10 days of cultivation; FIG. 3C, Example 3). In addition, EBs generated according to the present teachings are round, small (e.g., having a diameter of 358±135 μm) and homogenous (FIGS. 2A-F; Example 2), with normal karyotype and metabolism indices (Example 3), devoid of necrotic centers (Example 3), with insignificant percentage of apoptotic cells (up to 4%; FIGS. 3E-I, Example 3), and express markers of all three embryonic germ cell layers (FIGS. 4A-I, FIGS. 5A-K; Example 4). Moreover, as shown in Example 5 of the Examples section which follows, the EBs generated according to the present teachings were capable of differentiation into cardiomyocytes, contracting EBs (e.g., over 30% contracting EBs obtained after 10 days of cultivation; FIGS. 6A-F) and to endothelial cells (FIGS. 7A-H, FIGS. 8A-C) and thus can be used for various therapeutic applications.

Thus, according to one aspect of the invention, there is provided a method of generating embryoid bodies. The method is effected by (a) culturing embryonic stem cells under static conditions; and subsequently (b) culturing the embryonic stem cells under dynamic conditions which are further described below.

As used herein the phrase "embryoid bodies" (EBs) refers to three-dimensional multicellular aggregates of differentiated and undifferentiated cells derivatives of three embryonic germ layers.

The phrase "embryonic stem cells" refers to embryonic cells which are capable of differentiating into cells of all three embryonic germ layers (i.e., endoderm, ectoderm and mesoderm), or remaining in an undifferentiated state. The phrase "embryonic stem cells" may comprise cells which are obtained from the embryonic tissue formed after gestation (e.g., blastocyst) before implantation of the embryo (i.e., a pre-implantation blastocyst); extended blastocyst cells (EBCs) which are obtained from a post-implantation/pre-gastrulation stage blastocyst (see WO2006/040763); embryonic germ (EG) cells which are obtained from the genital tissue of a fetus any time during gestation, preferably before 10 weeks of gestation; and induced pluripotent stem cells (iPS; embryonic-like stem cells), which are obtained by de-differentiation of adult somatic cells which are endowed with pluripotency (i.e., being capable of differentiating into the three embryonic germ cell layers, i.e., endoderm, ectoderm and mesoderm) by genetic manipulation which re-program the cell to acquire embryonic stem cells characteristics (e.g., by inducing the expression of Oct-4, Sox2, Kfl4 and c-Myc in a somatic stem cell). In an exemplary embodiment, the ESCs used by the invention are derived from a human or primate (e.g., monkey), rodent (e.g., rat, mouse) origin.

According to some embodiments of the invention, the ESCs are human ESCs.

Human ESCs can be purchased from the NIH human embryonic stem cells registry (http://escr.nih.gov). Non-limiting examples of commercially available embryonic stem cell lines are BG01, BG02, BG03, BG04, CY12, CY30, CY92, CY10, TE03 and TE32.

As used herein, the term "culturing" refers to seeding ESCs in a culture vessel containing medium suitable for EBs formation and subjecting them to the appropriate culturing temperatures (e.g., 37° C.), supply of oxygen and other gasses.

A non-limiting example of a medium suitable for EBs formation comprises 80% KO-DMEM, 20% serum, 1% Penicillin-Streptomycin, 1 mM L-glutamine, and 1% non-essential amino acid stock.

Prior to seeding in the culture vessel, the ESCs are removed from their feeder cell layers (e.g., foreskin fibroblasts, mouse embryonic fibroblasts) or from feeder-free culture systems (e.g., fibronectin matrix, foreskin-fibroblast matrix, MATRIGEL). ESCs removal can be effected by various methods known in the art, such as with type IV Collagenase or Trypsin treatment for a limited time.

In addition, as shown in Example 1 of the Examples section which follows, ESCs are seeded in the form of initiation nucleus foci (INF) (i.e., aggregates of ESCs which are needed for the formation of EBs), which are obtained by mechanical breakdown of the hESC colonies. The size of the INF can be controlled by selecting a suitable tool, e.g., pipettes having tips of different diameters. For example, to obtain small INFs which include an average of 5±3 cells in each INF, a pipette tip of 100-μm diameter is used for intensive mechanical breakdown of the ESCs colonies. Alternatively, for large INFs which include an average of 1445±115 cells in each INF, the mechanical breakdown is performed using a pipette of 300-μm in diameter.

According to some embodiments of the invention, seeding of the ESCs is performed using an INF which comprises about 1300-1600 of the embryonic stem cells.

As shown in Example 1 of the Examples section which follows, the present inventors have demonstrated that seeding of about 0.3-1×10$^6$ ESCs per milliliter (ml) medium results in formation of EBs within 24 hours.

Thus, according to some embodiments of the invention, seeding is effected at a concentration of at least about 0.3×10$^6$ cells/ml, such as at least about 0.3×10$^6$ cells/ml, at least about 0.4×10$^6$ cells/ml, at least about 0.5×10$^6$ cells/ml, at least about 0.6×10$^6$ cells/ml, at least about 0.7×10$^6$ cells/ml, at least about 0.8×10$^6$ cells/ml, at least about 0.9×10$^6$ cells/ml, e.g., about 1×10$^6$ cells/ml.

According to some embodiments of the invention, seeding is effected at a concentration of ESCs which does not exceed 1.1×10$^6$ cells/ml.

According to some embodiments of the invention, seeding is effected at a concentration of ESCs of about 0.8×10$^6$ cells/ml medium.

As used herein, the phrase "static conditions" refers to culture conditions in which cells are kept in minimal motion conditions to reduce the shear forces acting thereupon. According to some embodiments of the invention, the static conditions enable differentiation of embryonic stem cells into EBs while preventing extensive EB agglomeration (aggregates of two or more EBs).

The cells can be placed in non-adherent or non-coated dishes [e.g., Petri dish and the Rotating Wall Vessel (RWV) bioreactors developed by NASA (U.S. Pat. Nos. 5,763,279 and 5,437,998 to Schwartz et al) such as the Slow Turning Lateral Vessel (STLV), which includes a tubular shaped chamber with a central gas transfer cord] under static conditions.

According to some embodiments of the invention, the static conditions include a diffusion mass transfer mechanism which enables transfer of gasses by diffusion alone.

As shown in the Examples section which follows, the present inventors have uncovered that culturing of ESCs for 2 days under static conditions prior to their transfer to dynamic conditions results in a high yield of EBs (e.g., 200-500 EBs/ml after 10 days in culture; FIGS. 1F-I, Example 1). In contrast, culturing of ESCs under static conditions for 1 day prior to their transfer to dynamic conditions results in a relatively low yield of EBs (Example 1), and culturing ESCs under static conditions for an extended period of time (e.g., 10 days) results in a high number of apoptotic cells, localized mostly in the center of the EBs (see FIGS. 3E and 3F, Example 3).

Thus, according to some embodiments of the invention, culturing of the ESCs under static conditions is effected for more than one day, e.g., for about two days, e.g., for about 3 or 4 days. According to some embodiments of the invention, culturing the ESCs under static conditions is effected for a time period which does not exceed about 4 days.

As used herein the phrase "dynamic conditions" refers to culturing conditions which result in spatial motion of the cell in culture. It will be appreciated that such spatial motion results in activation of shear forces on the cells, which significance to biological processes is well documented.

The shear forces employed on the ESCs in culture may affect the shape, size, viability, growth rate and/or yield of the generated EBs.

Thus, as shown in Example 3 of the Examples section which follows, EBs generated under dynamic conditions using a Paddle Impeller exhibit a significant apoptosis localized at the surface of the EBs (FIG. 3I). On the other hand, EBs generated under dynamic conditions using a Glass Bulb-shaped Impeller (GBI) (FIG. 3G) or a shaking Erlenmyer (FIG. 3H) exhibit only a few, dispersed apoptotic cells which are not localized at the surface or the center of the EBs.

Thus, according to some embodiments of the invention, the dynamic conditions comprise exposing the cells to lower shear forces as compared to the shear forces generated when stirring the cells with a paddle impeller.

The dynamic conditions can be achieved using a Glass Bulb-shaped Impeller (GBI). A GBI flask is a culture vessel equipped with a single or 2 glass pendula, each having a bulb-shape, which guarantee low shear forces while maintaining optimum mixing. The GBI flask can be of any size, depending on the intended use. For example, currently available GBI flasks are of 100 ml, 250 ml, 500 ml, 1000 ml or 3000 ml (e.g., Integra Catalogue numbers 182023, 182026, 182051, 182101 for GBI flasks, or Integra Catalogue numbers 182701, 182703, and 182706 for Glass pendula; Cell-Spin systems of Integra Biosciences, Fernwald, Germany). The volume of medium filled in the GBI flask can vary, e.g., a 500 ml GBI flask may be filled with about 55-250 ml of medium; a 3-Liter GBI flask can be filled with up to 1.5 liter of medium.

According to some embodiments of the invention, stirring of the GBI is effected by a mixing rate in about 30-75 rounds per minute.

Alternatively, suitable dynamic conditions are achieved by externally shaking or agitating a culture vessel containing the ESCs, such as by placing the culture vessel on an externally agitating device, e.g., a rotary shaker, capable of creating fluid rotational motion in the culture vessel. For example, the shaker can be an orbital shaker having a flat table or platform which is moved in a circular gyratory motion (on a single horizontal plane or several planes). Alternatively, the agitation can be on a single axis (axially).

According to some embodiments of the invention, the agitation is performed using an orbital shaker.

Non-limiting examples of suitable culture vessels include an Erlenmeyer flask, T-flask, tissue culture plates (e.g., 6-well plate) and a Fernbach flask.

According to some embodiments of the invention, the culture vessel is an Erlenmeyer flask. The size of the Erlenmeyer flask can be from 125-5000 ml, e.g., a 125-ml flask which can be filled with 25 ml of medium. The volume of culture medium contained within the culture vessel (also referred herein as a "working volume") can be between 15-20% of the total volume of the culture vessel. According to some embodiments of the invention, the Erlenmeyer is agitated at a rate of 95-150 rounds per minute (RPM), e.g., about 105±10 RPM for an Erlenmyer with a volume of 125 ml. It should be noted that the agitation rate can be adjusted according to the size of culture vessel used.

According to some embodiments of the invention, the dynamic conditions used by the method of the invention are selected capable of generating EBs which include no more than about 7%, no more than about 6%, no more of about 5%, e.g., no more than about 4% of apoptotic cells following 10 days in culture (or 8 days under dynamic conditions).

According to some embodiments of the invention, the dynamic conditions employed are selected capable of preventing massive apoptosis localized at the center or the surface of the EBs, and/or preventing necrotic centers within the EBs.

As mentioned, the dynamic conditions used for culturing may affect the viability, growth rate and expansion capacity of the cells.

According to some embodiments of the invention, the dynamic conditions enable at least about 4.8, at least about 5, at least about 5.2, at least about 5.4, at least about 5.5, at least about 5.6, at least about 5.8, at least about 6, at least about 6.2, at least about 6.4, at least about 6.5, at least about 6.7 fold expansion of the embryonic stem cells following six days of culture in the dynamic conditions.

According to some embodiments of the invention, the dynamic conditions enable high viability of cells within the EBs, such as at least about $3.3 \times 10^6$ viable cells/ml, at least about $3.5 \times 10^6$ viable cells/ml, at least about $3.7 \times 10^6$ viable cells/ml, at least about $3.9 \times 10^6$ viable cells/ml, at least about $4 \times 10^6$ viable cells/ml, at least about $4.2 \times 10^6$ viable cells/ml, at least about $4.4 \times 10^6$ viable cells/ml, at least about $4.6 \times 10^6$ viable cells/ml, at least about $4.8 \times 10^6$ viable cells/ml, at least about $5 \times 10^6$ viable cells/ml following 8 days in culture (or 6 days under dynamic culture conditions).

According to some embodiments of the invention, the dynamic conditions enable a logarithmic growth of viable cells with a growth rate ($\mu$) of at least about 1.6 day$^{-1}$, at least about 1.7 day$^{-1}$, at least about 1.8 day$^{-1}$, at least about 1.9 day$^{-1}$, at least about 2 day$^{-1}$, at least about 2.1 day$^{-1}$, at least about 2.2 day$^{-1}$, at least about 2.3 day$^{-1}$ during 8 days in culture (or 6 days under dynamic culture conditions).

During the culturing period, the cells forming the EBs are measured (e.g., shape, diameter) and monitored for cell metabolism, karyotype, and differentiation state.

As described in Example 2 of the Examples section which follows, following 10 days in culture (8 days under dynamic conditions), EBs generated using the Erlenmeyer (FIG. 2C) or GBI (FIG. 2D) spinner flasks exhibit diameters of 375±93 µm and 358±135 µm, respectively (FIG. 2F). In contrast, EBs generated in the PI spinner flask (10 days in culture of them 8 days in dynamic conditions) had irregular shapes (FIG. 2E) and a diameter of 488±193 µm (FIG. 2F), similar to EBs generated under static conditions (for 10 days) in Petri dish (FIG. 2A) or RWV bioreactor (FIG. 2B) which exhibited irregular shapes and diameters of 564±223 µm and 491±243 µm, respectively (FIG. 2F).

According to some embodiments of the invention, the dynamic conditions are selected suitable for forming small, homogenous EBs, having an average diameter which does not exceed about 400 µm.

According to some embodiments of the invention, at least about 90%, e.g., at least about 95%, e.g., at least about 99% (e.g., 100%) of the embryoid bodies generated according to the teachings of the invention exhibit a round shape.

As shown in Example 3 of the Examples section which follows, metabolic indices, such as glucose and glutamine consumption, lactic acid production, lactate dehydrogenase (LDH) secretion and pH, pointed to efficient cell expansion in the stirred cultures.

Cell differentiation can be determined upon examination of cell or tissue-specific markers. For example, the differentiation level of the EB cells can be monitored by following the loss of expression of Oct-4, and the increased expression level of markers such as neurofilament 68 KD and NeuroD1 for the ectoderm, CD 34 and CMP for the mesoderm, and glucagon and GLUT2 for the endoderm. Methods useful for monitoring the expression level of specific genes are well known in the art and include RT-PCR, semi-quantitative RT-PCR, Real-Time RT-PCR, Northern blot, RNA in situ hybridization, Western blot analysis and immunohistochemistry.

As shown in FIGS. 6A-B and described in Example 5 of the Examples section which follows, EBs generated using the present teachings are capable of spontaneous differentiation into cardiomyocytes. For example, when the EBs were removed at day 4 of culture (following 2 days under dynamic conditions) and were further cultured for 15 days on Gelatin-coated Petri dishes, 35% of the EBs cultured using the GBI stirred flasks spontaneously contracted. In addition, as shown in FIG. 6C EBs generated using the GBI dynamic conditions were found to express high levels of α-myosin heavy chain (α-MHC). Moreover, as shown in FIGS. 7A-H and described in Example 5 of the Examples section which follows, when 10-day old EBs were removed from the suspension culture and were allowed to attach to gelatin-coated slides, a well developed capillary network in the whole EBs was observed.

Thus, according to another aspect of the invention there is provided a method of generating expanded and/or differentiated cells from embryonic stem cells. The method is effected by isolating lineage specific cells from the EBs of the invention and culturing the lineage specific cells under culturing conditions selected suitable for the expansion and/or differentiation of the lineage specific cells to thereby obtain expanded and/or differentiated lineage-specific cells.

As used herein, the phrase "isolating lineage specific cells" refers to the enrichment of a mixed population of cells in a culture with cells predominantly displaying at least one characteristic associated with a specific lineage phenotype. It will be appreciated that all cell lineages are derived from the three embryonic germ layers. Thus, for example, hepatocytes and pancreatic cells are derived from the embryonic endoderm, osseous, cartilaginous, elastic, fibrous connective tissues, myocytes, myocardial cells, bone marrow cells, vascular cells (namely endothelial and smooth muscle cells), and hematopoietic cells are differentiated from embryonic mesoderm and neural, retina and epidermal cells are derived from the embryonic ectoderm.

According to some embodiments of the invention, isolating is effected by sorting of cells of the EBs via fluorescence activated cell sorter (FACS).

Methods of isolating EB-derived-differentiated cells via FACS analysis are known in the art. According to one method, EBs are disaggregated using a solution of Trypsin and EDTA (0.025% and 0.01%, respectively), washed with 5% fetal bovine serum (FBS) in phosphate buffered saline (PBS) and incubated for 30 minutes on ice with fluorescently-labeled antibodies directed against cell surface antigens characteristics to a specific cell lineage. For example, endothelial cells are isolated by attaching an antibody directed against the platelet endothelial cell adhesion molecule-1 (PECAM1) such as the fluorescently-labeled PECAM1 antibodies (30884x) available from PharMingen (PharMingen, Becton Dickinson Bio Sciences, San Jose, Calif., USA) as described in Levenberg, S. et al., (Endothelial cells derived from human embryonic stem cells. Proc. Natl. Acad. Sci. USA. 2002. 99: 4391-4396). Hematopoietic cells are isolated using fluorescently-labeled antibodies such as CD34-FITC, CD45-PE, CD31-PE, CD38-PE, CD9O-FITC, CD117-PE, CD15-FITC, class I-FITC, all of which IgG1 are available from PharMingen, CD133/1-PE (IgG1) (available from Miltenyi Biotec, Auburn, Calif.), and glycophorin A-PE (IgG1), available from Immunotech (Miami, Fla.). Live cells (i.e., without fixation) are analyzed on a FACScan (Becton Dickinson Bio Sciences) by using propidium iodide to exclude dead cells with either the PC-LYSIS or the CELLQUEST software. It will be appreciated that isolated cells can be further enriched using magnetically-labeled second antibodies and magnetic separation columns (MACS, Miltenyi) as described by Kaufman, D. S. et al., (Hematopoietic colony-forming cells derived from human embryonic stem cells. Proc. Natl. Acad. Sci. USA. 2001, 98: 10716-10721).

According to some embodiments of the invention, isolating is effected by a mechanical separation of cells, tissues and/or tissue-like structures contained within the EBs.

For example, beating cardiomyocytes can be isolated from EBs as disclosed in U.S. Pat. Appl. No. 20030022367 to Xu et al.; and in U.S. Pat. Appl. No. 2005-0037489 A1 to Gepstein L. Four-day-old EBs of the present invention are transferred to gelatin-coated plates or chamber slides and are allowed to attach and differentiate. Spontaneously contracting cells, which are observed from day 8 of differentiation, are mechanically separated and collected into a 15-mL tube containing low-calcium medium or PBS. Cells are dissociated using Collagenase B digestion for 60-120 minutes at 37° C., depending on the Collagenase activity. Dissociated cells are then resuspended in a differentiation KB medium (85 mM KCl, 30 mM $K_2HPO_4$, 5 mM $MgSO_4$, 1 mM EGTA, 5 mM creatine, 20 mM glucose, 2 mM $Na_2ATP$, 5 mM pyruvate, and 20 mM taurine, buffered to pH 7.2, Maltsev et al., Circ. Res. 75:233, 1994) and incubated at 37° C. for 15-30 min. Following dissociation cells are seeded into chamber slides and cultured in the differentiation medium to generate single cardiomyocytes capable of beating.

According to some embodiments of the invention, isolating is effected by subjecting the EBs to differentiation factors to thereby induce differentiation of the EBs into lineage specific differentiated cells.

Following is a non-limiting description of a number of procedures and approaches for inducing differentiation of EBs to lineage specific cells.

Neural precursor cells—To differentiate the EBs of the present invention into neural precursors, four-day-old EBs are cultured for 5-12 days in tissue culture dishes including DMEM/F-12 medium with 5 mg/ml insulin, 50 mg/ml transferrin, 30 nM selenium chloride, and 5 mg/ml fibronectin (ITSFn medium, Okabe, S. et al., 1996, Mech. Dev. 59: 89-102). The resultant neural precursors can be further transplanted to generate neural cells in vivo (Brüstle, O. et al., 1997. In vitro-generated neural precursors participate in mammalian brain development. Proc. Natl. Acad. Sci. USA. 94: 14809-14814). It will be appreciated that prior to their transplantation, the neural precursors are trypsinized and triturated to single-cell suspensions in the presence of 0.1% DNase.

Generation of neuroepithelial cells—The EBs derived cells can be induced to differentiate with retinoic acid to form neuronal and glial precursors, positive for astrocyte (GFAP) or oligodendrocyte markers, then later into functional neurons (see, e.g., Fraichard, J Cell Science 108:3161-3188, 1995). Cells transplanted to adult brains were observed innervating the host striatum (Deacon, Exp. Neurology, 149:28-41, 1998). For example, neuroepithelial stem cells can be generated by replating the EBs in insulin-transferrin-selenium-fibronectin (ITSN) supplemented medium, culturing the cells for 6 to 7 days in the same medium, dissociating and re-plating into medium containing basic fibroblast growth factor (bFGF). Upon removal of FGF, neurons, astrocytes, and oligodendrocytes are expected to form in situ.

Oligodendrocytes and myelinate cells—EBs of the present invention can differentiate to oligodendrocytes and myelinate cells by culturing the cells in modified SATO medium, i.e., DMEM with bovine serum albumin (BSA), pyruvate, progesterone, putrescine, thyroxine, triiodothryonine, insulin, transferrin, sodium selenite, amino acids, neurotrophin 3, ciliary neurotrophic factor and Hepes (Bottenstein, J. E. & Sato, G. H., 1979, Proc. Natl. Acad. Sci. USA 76, 514-517; Raff, M. C., Miller, R. H., & Noble, M., 1983, Nature 303: 390-396]. Briefly, EBs are dissociated using 0.25% Trypsin/EDTA (5 min at 37° C.) and triturated to single cell suspensions. Suspended cells are plated in flasks containing SATO medium supplemented with 5% equine serum and 5% fetal calf serum (FCS). Following 4 days in culture, the flasks are gently shaken to suspend loosely adhering cells (primarily oligodendrocytes), while astrocytes are remained adhering to the flasks and further producing conditioned medium. Primary oligodendrocytes are transferred to new flasks containing SATO medium for additional two days. Following a total of 6 days in culture, oligospheres are either partially dissociated and resuspended in SATO medium for cell transplantation, or completely dissociated and a plated in an oligosphere-conditioned medium which is derived from the previous shaking step [Liu, S. et al., (2000). Embryonic stem cells differentiate into oligodendrocytes and myelinate in culture and after spinal cord transplantation. Proc. Natl. Acad. Sci. USA. 97:6126-6131].

Mast cells—For mast cell differentiation, two-week-old EBs of the present invention are transferred to tissue culture dishes including DMEM medium supplemented with 10% FCS, 2 mM L-glutamine, 100 units/ml penicillin, 100 mg/ml streptomycin, 20% (v/v) WEHI-3 cell-conditioned medium and 50 ng/ml recombinant rat stem cell factor (rrSCF, Tsai, M. et al., 2000. In vivo immunological function of mast cells derived from embryonic stem cells: An approach for the rapid analysis of even embryonic lethal mutations in adult mice in vivo. Proc. Natl. Acad. Sci. USA. 97: 9186-9190). Cultures are expanded weekly by transferring the cells to new flasks and replacing half of the culture medium.

Hemato-lymphoid cells—To generate hemato-lymphoid cells from the EBs of the present invention, 2-3 days-old EBs are transferred to gas-permeable culture dishes in the presence of 7.5% $CO_2$ and 5% $O_2$ using an incubator with adjustable oxygen content. Following 15 days of differentiation, cells are harvested and dissociated by gentle digestion with Collagenase (0.1 unit/mg) and Dispase (0.8 unit/mg), both are available from F. Hoffman—La Roche Ltd, Basel, Switzerland. CD45-positive cells are isolated using anti-CD45 monoclonal antibody (mAb) M1/9.3.4.HL.2 and paramagnetic microbeads (Miltenyi) conjugated to goat anti-rat immunoglobulin as described in Potocnik, A. J. et al., (Immunology Hemato-lymphoid in vivo reconstitution potential of subpopulations derived from in vitro differentiated embryonic stem cells. Proc. Natl. Acad. Sci. USA. 1997, 94: 10295-10300). The isolated CD45-positive cells can be further enriched using a single passage over a MACS column (Miltenyi).

Cardiomyocytes—EBs can be induced to differentiate in vitro to form cardiomyocytes (see, e.g., Wobus, Differentiation 48:173-182, 1991; Maltsev, Mech. Dev. 44:41-50, 1993; Klug, J. Clin. Invest. 98:216-224, 1996) and as described in Example 5 of the Examples section which follows.

Skeletal muscle cells—Skeletal muscle cells can be generated from the EBs by in vitro induction in the presence of about $10^{-8}$ to $10^{-7}$ M retinoic acid (see, e.g., Wobus, Roux's Arch. Dev. Biol. 204:36-45, 1994). Alternatively, stable transfection of EB cells with MyoD1 in the presence of DMSO can result in efficient formation of skeletal muscle (see, e.g., Dinsmore, Cell Transplant 5:131-143, 1996).

Generation of Neuromuscular Junctions—Co-culturing of skeletal myocytes generated from EB cells with neurons (e.g., which can be generated from the EBs as described above) can result in neuromuscular junctions. Neuromuscular junctions are specialized synapses connecting nerves and muscles. They are the target of chemical and biological toxins; e.g., inhibitors of the enzyme acetylcholinesterase, which is normally responsible for the degradation of the neurotransmitter acetylcholine, thereby attenuating the stimulation of the muscle by the nerve. The cells of the neuromuscular junction exhibit measurable electrical membrane potentials and depolarization events that are extremely sensitive to perturbations in their micro-environments. Using the EB-derived cells and cell lines of the invention, neuromuscular junctions that are anatomically uniform can be produced in constant supply without any substantial drift in performance characteristics or sensitivity. Because they are of human origin, they represent the appropriate distribution of membrane receptors and biological response patterns characteristic of human beings. The neuromuscular junctions can be used, inter alia, to detect toxins, study diseases, and screen for drugs.

Generation of Neuronal Networks—EBs can be used to generate neuronal networks using methods analogous to those used to generate networks from dissociated mouse embryos. Mouse neural networks were created on microelectrode arrays; these networks showed coordinated and quasi-periodic firing patterns that responded to the presence of pharmacological agents by altering both the amplitude and the frequency of the burst patterns (see, e.g., Gopal, Acta Otolaryngol. 116:690 696:697-704, 1996). The EBs-derived cells can form both excitatory and inhibitory synapses in culture; in mice, these synapses formed spontaneously upon differentiation (see, e.g., Finley, J. Neurosci. 16:10561065, 1996). The higher the density, the more frequent the likelihood of synapse formation. Neurons generated from the EB cells of the invention can be coupled with microelectrode arrays using standard methods and materials. These neuronal cells are expected to form functioning neural networks. Such networks can be used to screen for pharmacological agents and disease states.

Additional methods of generating lineage-specific cells from EBs are described in WO 01/53465 which is fully incorporated herein by reference.

It will be appreciated that the culturing conditions suitable for the differentiation and expansion of the isolated lineage specific cells include various tissue culture medium, growth factors, antibiotic, amino acids and the like and it is within the capability of one skilled in the art to determine which conditions should be applied in order to expand and differentiate particular cell types and/or cell lineages.

In addition to the lineage-specific primary cultures, EBs of the invention can be used to generate lineage-specific cell lines which are capable of unlimited expansion in culture.

Cell lines of the invention can be produced by immortalizing the EB-derived cells by methods known in the art, including, for example, expressing a telomerase gene [e.g., *homo sapiens* telomerase (GenBank Accession No: NM_003219) or mouse telomerase (GenBank Accession Nos: AF051911, AF073311)] in the cells (Wei, W. et al., 2003. Abolition of Cyclin-Dependent Kinase Inhibitor p16Ink4a and p21Cip1/Waf1 Functions Permits Ras-Induced Anchorage-Independent Growth in Telomerase-Immortalized Human Fibroblasts. Mol Cell Biol. 23: 2859-2870) or co-culturing the cells with NIH 3T3 hph-HOX11 retroviral producer cells (Hawley, R. G. et al., 1994. The HOX11 homeobox-containing gene of human leukemia immortalizes murine hematopoietic precursors. Oncogene 9: 1-12).

Since the lineage-specific cells of the invention are developed by differentiation processes similar to those naturally occurring in the human embryo they can be further used for human cell-based therapy and tissue regeneration.

Thus, according to another aspect of the invention there is provided a method of treating a disorder requiring cell replacement therapy. The method according to this aspect of the invention is effected by administering the expanded and/or differentiated lineage-specific cells of the invention to an individual in need thereof thereby treating the disorder requiring cell replacement therapy.

The phrase "treating" refers to inhibiting or arresting the development of a disease, disorder or condition and/or causing the reduction, remission, or regression of a disease, disorder or condition in an individual suffering from, or diagnosed with, the disease, disorder or condition. Those of skill in the art will be aware of various methodologies and assays which can be used to assess the development of a disease, disorder or condition, and similarly, various methodologies and assays which can be used to assess the reduction, remission or regression of a disease, disorder or condition.

As used herein "disorder requiring cell replacement therapy" refers to a neurological disorder, a muscular disorder, a cardiovascular disorder, an hematological disorder, a skin disorder (e.g., burn), a bone disorder, a cartilage disorder, a pancreatic disorder, a liver disorder, and the like that require cell replacement.

As used herein, "administering" refers to means for providing the expanded and/or differentiated lineage specific cells to an individual, using any suitable route, e.g., oral, sublingual, intravenous, subcutaneous, transcutaneous, intramuscular, intracutaneous, intrathecal, intra peritoneal, intra spleenic, intra hepatic, intra pancreatic, intra cardiac, epidural, intraoccular, intracranial, inhalation, rectal, vaginal, and the like administration.

The expanded and/or differentiated lineage specific cells can be encapsulated prior to their administration into the individual. Encapsulation techniques are generally classified as microencapsulation, involving small spherical vehicles and macroencapsulation, involving larger flat-sheet and hollow-fiber membranes (Uludag, H. et al. Technology of mammalian cell encapsulation. Adv. Drug Deliv. Rev. 2000; 42: 29-64). Methods of preparing microcapsules are known in the arts and include for example those disclosed by Lu M Z, et al., Cell encapsulation with alginate and alpha-phenoxycinnamylidene-acetylated poly(allylamine). Biotechnol. Bioeng. 2000, 70: 479-83, Chang T M and Prakash S. Procedures for microencapsulation of enzymes, cells and genetically engineered microorganisms. Mol. Biotechnol. 2001, 17: 249-60, and Lu M Z, et al., A novel cell encapsulation method using photosensitive poly(allylamine alpha-cyanocinnamylideneacetate). J. Microencapsul. 2000, 17: 245-51.

Differentiated stem cells of lineage specific origin can be utilized in treating various disorders. For example, oligodendrocyte precursors can be used to treat myelin disorders (Repair of myelin disease: Strategies and progress in animal models. Molecular Medicine Today. 1997. pp. 554-561), chondrocytes or mesenchymal cells can be used in treatment of bone and cartilage defects (U.S. Pat. No. 4,642,120) and cells of the epithelial lineage can be used in skin regeneration of a wound or burn (U.S. Pat. No. 5,716,411).

For certain disorders, such as genetic disorders in which a specific gene product is missing [e.g., lack of the CFTR gene-product in cystic fibrosis patients (Davies J C, 2002. New therapeutic approaches for cystic fibrosis lung disease. J. R. Soc. Med. 95 Suppl 41:58-67)], EBs-derived cells are preferably manipulated to over-express the mutated gene prior to their administration to the individual. It will be appreciated that for other disorders, the EBs-derived cells can be manipulated to exclude certain genes.

Over-expression or exclusion of genes can be effected using knock-in and/or knock-out constructs.

Knock-out and/or knock-in constructs can be used in somatic and/or germ cells gene therapy to destroy activity of a defective allele, gain of function (e.g., dominant) allele, or to replace the lack of activity of a silent allele in an individual, thereby down or up-regulating activity of specific genes, as required. Further detail relating to the construction and use of knockout and knock-in constructs can be found in Fukushige, S, and Ikeda, J. E.: Trapping of mammalian promoters by Cre-lox site-specific recombination. DNA Res 3 (1996) 73-50; Bedell, M. A., Jerkins, N. A. and Copeland, N. G.: Mouse models of human disease. Part I: Techniques and resources for genetic analysis in mice. Genes and Development 11 (1997) 1-11; Bermingham, J. J., Scherer, S. S., O'Connell, S., Arroyo, E., Kalla, K. A., Powell, F. L. and Rosenfeld, M. G.: Tst-1/Oct-6/SCIP regulates a unique step in peripheral myelination and is required for normal respiration. Genes Dev 10 (1996) 1751-62, which are incorporated herein by reference.

EBs and cells, tissues, structures and organs derived therefrom according to the present teachings can be used for toxicological, mutagenic, teratogenic in vitro tests and/or as biosensors. Thus, the invention provides engineered cells, tissues and organs for screening methods to replace animal models and form novel human cell-based tests. These systems are useful as extreme environment biosensors. EB cells or cell lines of the invention and cells, tissues, structures and organs derived therefrom can be used to build physiological biosensors; for example, they can be incorporated in known system, as described, e.g., in U.S. Pat. Nos. 6,130,037; 6,129,896; and 6,127,129. These sensors can be implanted bio-electronic devices that function as in vivo monitors of metabolism and other biological functions, or as an interface between human and computer.

The biosensor provided by the invention can also be used to screen for, or warn of, environmental toxins or exposure to dangerous chemicals. In one embodiment, the above-described biosensor is exposed to environmental substances (e.g., air, water, soil), or to samples derived therefrom, and the response of the biosensor is monitored. If a dangerous agent is detected, the response of the system to the agent can be recorded for evaluation, a portion of the sample can be isolated for further study, and an alarm sounded.

The EBs derived cells of the invention can be used to qualify the effect of a treatment on a biological state or a biological process e.g., of cardiac cells or cardiac tissue. Qualifying the effect of a treatment on a biological state or a biological process of the cells and tissues of present invention, for example an abnormal biological state or process thereof, can be used to identify and optimize treatments capable of restoring the normal biological state or process, and hence can be used to identify and optimize treatments suitable for treating a disorder (e.g., cardiac disorder). Furthermore, qualifying the effect of a treatment on a biological state or a biological process of cells or tissues can be used to assess the toxicity of such a treatment on such a biological state or process. The EBs and cells derived therefrom can be used to assess the embryotoxicity of a treatment, in particular a treatment with a compound. For example, failure to generate a characteristic associated with a cardiac phenotype, preferably cardiac specific mechanical contraction, in the cells and tissues of the present invention in response to treatment with a compound can be used to qualify the embryotoxicity, such as the cardiac specific or systemic embryotoxicity, of such a compound.

The lineage specific cells of the invention can be used to screen for factors (such as small molecule drugs, peptides, polynucleotides, and the like) or conditions (such as culture conditions or manipulation) that affect the differentiation of lineage precursor to terminally differentiated cells. For example, growth affecting substances, toxins or potential differentiation factors can be tested by their addition to the culture medium.

In addition, the lineage specific cells of the invention can also be utilized to prepare a cDNA library. mRNA is prepared by standard techniques from the lineage specific cells and is further reverse transcribed to form cDNA. The cDNA preparation can be subtracted with nucleotides from embryonic fibroblasts and other cells of undesired specificity, to produce a subtracted cDNA library by techniques known in the art.

As used herein the term "about" refers to ±10%

The terms "comprises", "comprising", "includes", "including", "having" and their conjugates mean "including but not limited to".

The term "consisting of means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683, 202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed.

(1984); "Nucleic Acid Hybridization" Hames, B. D., and Higgins S. J., eds. (1985); "Transcription and Translation" Hames, B. D., and Higgins S. J., Eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

General Materials and Experimental Methods

Culture of hESCs—Human embryonic stem cells (hESCs), cell line H9.2, passages 38-61, were cultured on a mitomycin C (Sigma, St. Louis, Mo., USA) inactivated mouse embryonic fibroblast (MEF) feeder layer as previously described (Amit M, Carpenter M K, Inokuma M S, Chiu C P, Harris C P, Waknitz M A, Itskovitz-Eldor J and Thomson J A. (2000) Clonally derived human embryonic stem cell lines maintain pluripotency and proliferative potential for prolonged periods of culture. Dev Biol. 227:271-8). Briefly, cells were maintained in growth medium consisting of 80% KNOCKOUT® DMEM, 20% [volume/volume (v/v)] KNOCKOUT® serum replacement (SR), 1 mM glutamine, 0.1 mM-2-mercaptoethanol, 1% nonessential amino acids, and 4 ng/ml basic fibroblast growth factor (bFGF) (all from Gibco Invitrogen Corporation, Grand Island, N.Y., USA), the medium was changed daily. Under these conditions cells were kept undifferentiated. For passaging, the cells were harvested every 4-6 days by treatment with 0.2% collagenase type IV (Whorthington Biochemical Corporation, Lakawood, N.J., USA) followed by mechanical dissociation to achieve small cell aggregates, and reseeded on freshly prepared MEF feeders.

EB propagation in stirred systems—Undifferentiated hESCs grown to confluency were used to induce EB formation. The cells were removed from their feeder layer by treatment with 0.2% collagenase type IV (Whorthington Biochemical Corporation, Lakawood, N.J., USA) and dispersed into small clumps. Cells were seeded at an initial concentration of $0.7 \pm 0.1 \times 10^6$ hESCs/ml and initiation nucleation foci (INF) size of a 1445±115 cells/INF into the following static culture systems (with insignificant shear forces): the Rotating Wall Vessel (RWV) bioreactor [55 ml RWV/STLV bioreactor (Synthecon Incorporated, Houston, Tex., USA)] or Petri dishes [8 ml static non-adherent Petri dish (Miniplast, Ein Shemer, Israel)]. Two-day old EBs generated in the static culture systems (RWV or Petri dish) were seeded into the following stirred systems: 125 ml Erlenmeyer (Corning Incorporated, Corning N.Y., USA) with orbital shaking; 250 ml GBI spinner flask (CellSpin of Integra Biosciences, Fernwald, Germany); or 100 ml PI spinner flask (Bellco, Vineland, N.J., USA); or were remained for further culturing in the static culture systems.

During the ten-day cultivation period, 80±5% of the EBs growth medium was replaced every second day (see Table 1, hereinbelow for systems working volume). The EBs' culture medium consisting of 80% KNOCKOUT® DMEM (Gibco Invitrogen Corporation, Grand Island, N.Y., USA) supplemented with 20% fetal calf serum (FCS) (Biological Industries, Beit Haemek, Israel), 1% penicillin-streptomycin (Biological Industries, Beit Haemek, Israel), 1 mM L-glutamine and 1% nonessential amino acid (all from Gibco Invitrogen Corporation, Grand Island, N.Y., USA).

Table 1, hereinbelow provides operation parameters (i.e., working volume, mixing rates, etc.). Two independent experiments were performed in duplicates for each setting. EB formation was evaluated daily by light microscopy analysis for the period of up to ten days.

TABLE 1

Characterizations of EB culture systems

| Culture system | Total volume (ml) | Working volume (ml) | Mixing rate (rpm) | Mixing method |
|---|---|---|---|---|
| Static system - 19.6 cm$^2$ Petri dish | 10 | 8 | 0 | N.A. |
| Slow Turning Lateral Vessel (STLV) | 55 | 55 | 16 | Lateral turning |
| Spinner flask equipped with double Glass Bulb-shaped Impeller (GBI) | 250 | 55 | 75[1] | Agitation |
| Spinner flask equipped with Paddle-Impeller (PI) | 100 | 55 | 105 ± 10 | Agitation |
| Erlenmeyer | 125 | 25 | 105 ± 10 | Orbital shaking |

Table 1: EBs culture systems.
[1] = Maximum agitation rate available.

EB concentration, viable cell concentration and EB size— The EBs were harvested for analysis every second day at the time of medium change. Homogenously suspended EBs were removed in 1 ml growth medium and divided into five aliquots of 200 μl each. The number of EBs was counted to determine concentration for each experimental set up and average±SD (standard deviation) was calculated. In addition, homogenously suspended EBs were harvested in 1 ml growth medium, the medium was removed, and the EBs were incubated for 10 minutes with 0.5% Trypsin-EDTA (Gibco Invitrogen Corporation, Grand Island, N.Y., USA) and resuspended to achieve single cell suspension. Cells' concentration was measured by Coulter Counter Z2 (Beckman, USA) and by DNA contents test, average±SD was calculated. Cells' viability was determined by staining with 0.4 M trypan-blue solution (Sigma St. Louis, Mo., USA). All samples were prepared in duplicates and results are represented as mean values (±SD). For EB size and morphology analysis samples were transferred into culture dishes and analyzed using inverted light microscopy (Zeiss Axiovert 40C). The average diameter of 30 EBs in each system was calculated. Results are represented as mean values (±SD).

Apoptosis Detection-10-day-old EBs were analyzed for the presence of apoptotic cells using In Situ Cell Death Detection Kit, AP (Roche Diagnostics GmbH, Mannheim, Germany) according to manufacturer's instructions. Prior to application of quantitative staining protocol, EBs from 1 ml of homogenous suspension were incubated for 15 minutes with 200 μl 0.5% Trypsin-EDTA (Gibco Invitrogen Corporation, Grand Island, N.Y., USA) followed by re-suspension in 4 ml of Hanks solution (Sigma St. Louis, Mo., USA). Single cells were fixed on slides for staining. The number of apoptotic cells was determined by visual counting using the inverted fluorescent microscope (Zeiss Axiovert 200). Counting was performed in duplicates of 1000 cells per each experimental set up. Results are represented as average with mean values (±SD).

Whole EBs were analyzed for the localization of apoptotic cells. For this purpose, EBs were allowed to attach to 8 well slides (Nalge Nunc int., Rochester, N.Y., USA) and stained according to manufacturer's instructions (In Situ Cell Death Detection Kit, AP; Roche Diagnostics GmbH, Mannheim, Germany). Apoptotic cells were detected using a Nikon Eclipse E600 confocal microscope. Slides were stored at 2-8° C. before analysis.

Immunohistochemical analysis—For histological analysis, 10-day-old EBs were fixed in 10% neutral-buffered formalin, dehydrated by using graded alcohols (70-100%) and embedded in paraffin. For general morphology examination, 1-5 μm sections were stained with hematoxylin/eosin (Sigma St. Louis, Mo., USA). Immunostaining was performed using LSAB+ staining kit (DakoCytomation, Carpinteria, Calif., USA) according to manufacturer's instructions. Specific primary antibodies were used for detection of three germ layers: mouse anti-human Tubulin β-III (1:500, Chemicon International, Temecula, Calif., USA) for ectoderm, mouse anti-human CD34 (1:20) for mesoderm and rabbit anti-human α-fetoprotein (1:20) for endoderm (both from DakoCytomation, Glostrup, Denmark). Samples were analyzed using the Zeiss Axioskop 40 light microscope.

For fluorescent immunostaining of endothelial networks and cardiac cells, EBs were fixed with 4% Paraformaldehyde (Electron Microscopy Sciences, Hatfield, Pa.), 1% Triton (Sigma, St. Louis, Mo., USA) and 1% Triton+2% NGS in PBS. Samples were incubated for 12 hours at 4° C. with mouse anti-human CD31 (1:20; DakoCytomation, Glostrup, Denmark) and mouse anti-human Troponin I (1:800, Chemicon International, Temecula, Calif., USA) primary antibodies. Anti-mouse IgG I indocarbocyanine (Cy3) conjugated secondary antibody (1:50, Sigma, St. Louis, Mo., USA) was used. Vybrant® (Molecular Probes, Inc.) CM-Dil/TO-PRO-3 (1:500, Molecular Probes, Eugene, Oreg., USA) and DAPI (1:1000, Boehringer, Mannheim, Germany) were used for nuclear staining. Samples were analyzed using the Nikon Eclipse E600 confocal microscope and the Zeiss Axiovert 200 fluorescent microscope.

RT-PCR Analysis—Total RNA was isolated from 2-, 4-, 6-, 8- and 10-day-old EBs and undifferentiated hESCs using Tri-Reagent (Sigma, St. Louis, Mo., USA) according to the manufacturer's protocol. Complementary DNA was synthesized from 1 μg of total RNA using MMLV reverse transcriptase RNase H minus (Promega, Madison, Wis., USA). PCR primers and reaction conditions are provided in Table 2 below. PCR products were size-fractionated by electrophoresis on 2% agarose gel.

TABLE 2

PCR reaction conditions
PCR primers and conditions.

| Gene product | Forward (F) and reverse (R) primers (5' → 3') | Reaction condition | Size (base pairs) |
|---|---|---|---|
| Oct - 4 | F: GAGAACAATGAGAACCTTCAGGA; (SEQ ID NO: 1) R: TTCTGGCGCCGGTTACAGAACCA; (SEQ ID NO: 2) | 25 cycles at 55° C. in 1.5 mM MgCl$_2$ | 219 |
| Rex 1 | F: GCGTACGCAAATTAAAGTCCAGA; (SEQ ID NO: 3) R: CAGCATCCTAAACAGCTCGCAGAAT; (SEQ ID NO: 4) | 28 cycles at 56° C. in 1.5 mM MgCl$_2$ | 306 |
| NF-68 KD | F: GAGTGAAATGGCACGATACCTA; (SEQ ID NO: 5) R: TTTCCTCTCCTTCTTCACCTTC; (SEQ ID NO: 6) | 25 cycles at 60° C. in ready mix | 473 |
| NEUROD1 | F: CCTCGAAGCCATGAACGCAG; (SEQ ID NO: 7) R: GCTGTCCATGGTACCGTAAG; (SEQ ID NO: 8) | 35 cycles at 60° C. in ready mix | 583 |
| CMP | F: ACGGCTGACTTCAAGACCAT; (SEQ ID NO: 9) R: TCAATAGGCACACCCAGACA; (SEQ ID NO: 10) | 32 cycles at 60° C. in ready mix | 313 |
| CD34 | F: CAACACGTGGTGGCTGATAC; (SEQ ID NO: 11) R: TCAAAGCTTCCTGGGAGAAA; (SEQ ID NO: 12) | 35 cycles at 60° C. in 1.5 mM MgCl2 | 428 |
| Glucagon | F: AGGCAGACCCACTCAGTGA; (SEQ ID NO: 13) R: AACAATGGCGACCTCTTCTG; (SEQ ID NO: 14) | 40 cycles at 55° C.C. in ready mix | 308 |
| GLUT2 | F: AGGACTTCTGTGGACCTTATGTG; (SEQ ID NO: 15) R: GTTCATGTCAAAAAGCAGGG; (SEQ ID NO: 16) | 32 cycles at 55° C. in ready mix | 231 |

Real-Time RT-PCR Analysis—Total RNA was isolated from duplicate samples with Tri Reagent (Sigma, St. Louis, Mo., USA) and 1 μg of total RNA was used for reverse transcription by M-MLV RT (Promega, Madison, Wis., USA). Real Time PCR reactions were performed using the 7000 Sequence Detection system in triplicate for each one of both samples. The reactions were performed using TaqMan universal PCR master mix and primers from TaqMan gene expression assay (both from Applied Biosystems, Branchburg, N.J., USA). The primers used are: α-MHC (Catalogue No. HS00411908_m1, Applied Biosystems), VE-cadherin (Catalogue No. HS00174344_m1, Applied Biosystems), β-actin (Catalogue No. HS99999903_M1, Applied Biosystems). Each reaction well contained 5% of the cDNA sample (produced from 1 µg RNA). Relative quantification of gene expression was performed with the "7000 system SDS" software using β-actin as the internal control gene for normalization. The calculation of the relative quantification by this program was done by the $2^{-\Delta\Delta Ct}$ method [Livak K. J. and Schmittgen T. D., 2001, Analysis of relative gene expression data using real-time quantitative PCR and the 2(-Delta Delta C(T)) Method. Methods.25(4):402-8].

FACS Analysis—Single cell suspension was obtained from EBs by dissociation with EDTA splitting solution [99% phosphate buffered saline (PBS) (v/v), 1% defined fetal bovine serum (FBS), 0.5 mM EDTA, 0.1 mM-2-mercaptoethanol, all from Gibco Invitrogen Corporation, Grand Island, N.Y., USA] for 1.5 hour at 37° C., followed by mechanical disruption. Cells were washed and filtered through a 45 µm cell strainer (BD Bioscience, Bedford, Mass., USA). FACS analysis was performed using PE-conjugated anti-human VE-Cadherin/CD144 (1:2.5, R&D Systems, Inc., Minneapolis, Minn., USA) and FITC-conjugated anti-human CD31 (1:5, eBioscience, San Diego, Calif., USA) antibodies. Appropriate isotype antibodies were used as a control.

Spontaneous differentiation into cardiomyocytes—EBs from each experimental set up were seeded on a 6-well plate pre-coated with gelatin (10-30 EBs per well) and allowed to attach in order to accelerate the cardiomyocytic spontaneous differentiation [Kehat I., et al., 2001, Human embryonic stem cells can differentiate into myocytes with structural and functional properties of cardiomyocytes, J. Clin. Invest. 108(3):407-14; Xu C., et al., 2002, Characterization and enrichment of cardiomyocytes derived from human embryonic stem cells. Circ Res. 91(6):501-8]. EBs at two attachment time points were tested: 4-day old EBs and 7-day old EBs. Two milliliter per well of the same EB medium was replaced every second day and the contracting EBs were counted. The localization of EBs in each well was recorded manually.

Statistical analysis—All statistical analyses were performed using Student's t-test. All results, generated from at least two independent experiments, were analyzed using a significance level of p=0.05. The data are presented as the mean±SD.

Example 1

Optimization of Seeding and Culturing Conditions of Embryoid Bodies

To evaluate the potential advantages of stirred culture for human EB growth, three different stirred systems were compared to the RWV bioreactor and the static conventional suspension system (Petri-dish) at different seeding conditions. Three seeding parameters were tested: cell seeding concentration, shear force at seeding and initiation nucleation foci (INF) size, as follows.

Experimental Results

Determination of optimal hESCs concentration suitable for EBs' formation on static cultures—The effect of cell seeding concentration on EBs formation yield was determined by seeding hESCs on the static Petri-dish at various initial concentrations: 0.15, 0.3, 0.4, 0.6, 0.8 and $1.0\times10^6$ viable cells/ml. All initial cells seeding concentrations except $0.15\times10^6$ cells/ml concentration resulted in EB formation after 24 hours of incubation. Increasing of initial cell concentration up to $0.8\times10^6$ cells/ml yielded a higher EBs concentration. However, further increase in the initial cell concentration did not improve the EBs concentration (data not shown). Thus, concentration of $0.8\times10^6$ cells/ml was determined as the optimal seeding concentration.

Optimization of culture conditions for EBs' formation—In order to evaluate the efficiency of EB formation in stirred systems, hESCs were seeded into culture systems either directly after removal from the MEF feeder layer, or 1, 2, 4 or 6 days after EB formation in static Petri-dish. As is shown in FIGS. 1C-E, direct seeding of hESCs into stirred systems resulted in extensive EBs aggregation and low EBs concentration after 2-days of cultivation. In contrast, direct seeding into the RWV bioreactor (FIG. 1B) or Petri-dishes (FIG. 1A) had no such effect, probably due to the absence of shear forces. Initial formation of EBs in the Petri-dish for one day following by seeding into the stirred systems yielded a low number of EBs after 10 days of cultivation (data not shown). However, formation of EBs in static Petri-dishes for two days prior to seeding into the stirred Erlenmeyer and GBI spinner flask resulted in a very high EBs yield (200-500 EB/ml) after 10 cultivation days (FIGS. 1F-I).

Optimization of the size of initiation nucleation foci (INF) for EBs formation—To determine optimal INF size, 2 day old EBs formed in a Petri-dish were seeded into the stirred systems. Various INF sizes were obtained by mechanical breakdown of the hESC colonies, controlled by pipette diameter. Comparison was performed between small INF (average of 5±3 cells in each INF) obtained by intensive mechanical breakdown with 100 µm diameter pipette and large INF (average of 1445±115 cells in each INF) obtained by gentle mechanical breakdown with 300 µm diameter pipette.

After ten days of cultivation at mild shear forces stirred systems (Erlenmeyer and GBI spinner flask), the large INF size experimental group yielded up to 3-fold EB concentration as compared to the small INF size group (FIGS. 1F-I). Furthermore, EBs (formed from the large INF) propagated in the Erlenmeyer flasks demonstrated robust concentrations during the cultivation period: 489±22 EBs/ml at day of seeding to the Erlenmeyer vs. 479±98 EBs/ml at day 10 (data not shown). However, when seeded into the Petri dish, EBs' concentration in the small INF group was 2-fold higher as compared to the experimental group with large INF size (Compare FIG. 1I to FIG. 1G). The lowest final EBs concentration was observed at the PI spinner flask (84±56 EB/ml) and the RWV bioreactor (23±19 EB/ml) (FIG. 1G).

Example 2

Embryoid Bodies Cultured in Erlenmeyer and GBI Spinner Flasks are Homogenous and Exhibit a Round Shape Experimental Results EBs size distribution in stirred systems versus the RWV bioreactor and static systems—Round-shaped EBs were found after 10 days of cultivation in the Erlenmeyer (FIG. 2C) and GBI spinner flask (FIG. 2D), with diameters of 375±93 µm and 358±135 µm, respectively (FIG. 2F). In contrast, EBs grown in the Petri dish (FIG. 2A) and RWV bioreactor (FIG. 2B) exhibited irregular shapes and diameters of 564±223 µm and 491±243 µm, respectively (FIG. 2F). EBs grown in the PI spinner flask (FIG. 2E) had irregular shapes as well, with a diameter of 488±193 μm (FIG. 2F).

Example 3

Embryoid Bodies Cultured in Erlenmeyer and GBI Spinner Flasks Exhibit High Growth Rate, Viability and Survival Potential Experimental Results Growth kinetics and viability of cells in stirred systems compared to the RWV bioreactor and static system—In order to further characterize the propagation in the stirred systems, cell growth rate, cell viability, final viable cell concentration and percentage of apoptotic cells were analyzed and compared with the same parameters for RWV bioreactor and static Petri dish system. Cultivation in the GBI spinner flask yielded the highest viable cell concentration (e.g., $5.0 \times 10^6$ cells/ml on day 8 of culture; FIG. 3A) and the fastest growth rate of 2.3 per day ($2.3\ \text{day}^{-1}$). Cultivation in Erlenmeyer resulted in a concentration of $3.7 \times 10^6$ viable cells/ml on day 8 of culture (FIG. 3A) with growth rate of $1.9\ \text{day}^{-1}$, while in the PI spinner flask the lowest concentration ($2.7 \times 10^6$ cells/ml on day 8) and growth rate of $0.53\ \text{day}^{-1}$ were detected. Propagation in the RWV bioreactor also yielded a very low viable cells concentration ($1 \times 10^6$ cells/ml), and the slowest growth rate of $0.3\ \text{day}^{-1}$ was seen. In the Petri dishes concentration reached $3.2 \times 10^6$ viable cells/ml with a growth rate of $1.4\ \text{day}^{-1}$. The use of the GBI spinner flask and Erlenmeyer, as well as the static Petri dish, allowed logarithmic growth phase up to day 8 of cultivation followed by stationary phase (FIG. 3A).

The viability of cells in the Erlenmeyer and GBI spinner flasks was 90±1% for the whole cultivation period, similar to the cells grown in the Petri dish, while in the RWV bioreactor and PI spinner flask viability decreased during the first 4 days and then stabilized at 80% (FIG. 3B).

Metabolism analysis of cultivated EBs—Metabolism analysis detected no glucose and glutamine lack (minimum 2 gr/L and 1.2 mM, respectively) or lactate and ammonia accumulation (maximum 2 gr/L and >0.2 mM, respectively) within all cultivation systems and time periods. High LDH levels were found during the first two days of EB formation, probably caused by death of MEF and single hESCs. During the next eight days, the LDH concentrations remained at low level correlating with the cell viability results (data not shown).

Evaluation of survival potential of cultivated EBs—In order to evaluate survival potential at the end of the propagation phase, a percentage of apoptotic cells was determined. Specific staining of apoptotic cells was performed (1000 cells per sample) and it was found that less than 4% of the cells exhibited apoptosis in all the propagation systems, except for the cells grown in the RWV bioreactor (8%; FIG. 3D). No karyotype changes were found in the cells obtained from all experimental groups throughout the cultivation period. It should be noted that EBs generated in the GBI or shaking Erlenmyer stirred flasks were devoid of necrotic centers (FIGS. 3G-H and data not shown).

Evaluation of fold expansion of cultivated EBs—Cultivation in the GBI spinner flask supported the highest expansion fold (6.4) during 10 days of cultivation. In the Erlenmeyer, the expansion fold reached 4.8 and in the Petri dishes 4.0. The cells obtained from the PI spinner flask and RWV bioreactor exhibited expansion folds of 2.2 and 1.2, respectively (FIG. 3C).

Evaluation of apoptosis in cultivated EBs—Localization of apoptotic cells was performed by immunofluorescence staining of the whole EBs and visualized by confocal microscopy. Ten EBs were screened separately for each system. Random localization of few apoptotic cells was detected in EBs grown both in Erlenmeyer (FIG. 3G) and GBI spinner flasks (FIG. 3H) systems, while EBs grown in systems with diffusion mass transfer mechanism [i.e., static Petri dish (FIG. 3E) and RWV bioreactor (FIG. 3F)] presented a higher number of apoptotic cells, localized mostly in the center of the EBs. EBs obtained from PI spinner flask presented a high amount of apoptotic cells on the surface of the EB (FIG. 3I).

Example 4

Embryoid Bodies Cultured in the Stirred Cultures are Capable of Differentiation into all Three Embryonic Germ Cell Layers Experimental Results EBs potential to differentiate into representative cells of the three germ layers—Differentiation potential was examined for EBs formed in the GBI spinner flasks and the Erlenmeyer system where the EBs were exposed to shear stress throughout their formation and cultivation, and compared to EBs formed in the RWV bioreactor and the Petri dishes with no exposure to shear stress.

Expression of representative genes (markers) for each of the three germ layers was compared by RT-PCR: neurofilament 68 KD and NeuroD1 for the ectoderm, CD 34 and CMP for the mesoderm, and glucagon and GLUT2 for the endoderm. All of them were found positive. Transcription factors Oct-4 and Rex-1 expressed in undifferentiated hESCs were also examined. GAPDH served as an internal control. EBs obtained from both GBI and Erlenmeyer were found positive for markers of the three germ layers, and so were the EBs formed in the Petri dishes system (FIGS. 4A-I).

Histological sections were prepared from 10-day old EBs formed in the stirred systems, the RWV bioreactor and the Petri dish. Expression of Tubulin β-III, an ectodermal marker, was found in neuronal tubes formed inside the EBs (FIGS. 5A-D). CD34 positive cells were identified in newly formed capillary structures indicating mesodermal differentiation (FIGS. 5E-H). α-fetoprotein production was detected in early endoderm (FIGS. 5I-K). Morphological analysis of EBs obtained from stirred systems showed formation of endothelial cells positive for CD34, surrounding large primitive blood vessels, whereas examination of large neuronal rosettes revealed the Tubulin β-III positive cells. Altogether, this data indicate wide differentiation potential of the resulting EBs. Due to the low growth potential of the cells in the PI spinner flask, EBs from this system were not analyzed.

Example 5

Embryoid Bodies Cultured in the Stirred Cultures are Capable of Differentiation into Cardiomyocytes Experimental Results Evaluation of the differentiation into cardiomyocytes—Removal of EBs from the culturing systems at day 4 resulted in 35% contracting EBs in the GBI group and 18% in the Erlenmeyer group and the Petri dish after 15 days of spontaneous differentiation (FIG. 6A). Removal of EBs from the culture at day 7 resulted in lower percentage of contracting EBs after 15 differentiation days. EBs formed in the GBI spinner flask showed an advantage toward cardiomyocytic differentiation over all examined systems (FIG. 6B).

Quantitative evaluation of the cardiac specific α-MHC transcripts by real-time PCR showed obvious increase after four days within all systems (FIG. 6C). Six days after hESC seeding and EB formation α-MHC expression was two times higher in EBs obtained from the GBI spinner flask compared to the static system (400 vs. 200 RQ; FIG. 6C). Ten days after hESC seeding, EBs from the GBI spinner flask showed a 3-fold increase in α-MHC compared to the standard propagation condition in the static Petri dish, consistent with high percentage of contracting EBs shown in FIG. 6A. In order to examine the morphology of the beating regions, striated muscles contraction, which is detected only in the beating regions of the culture, was stained with cardiac-specific troponin I (cTnI). As shown in FIGS. 6D-F, a well developed representative cTnI-positive area was present within EBs from both stirring systems (FIGS. 6E and 6F) compared to static systems (FIG. 6D). Endothelial differentiation potential-10-day-old EBs were allowed to attach to gelatin-coated slides for two days, stained with anti CD31 antibody and analyzed using confocal microscopy. FIGS. 7A-H demonstrate a well developed capillary network in the whole EBs obtained from the stirred systems, RWV bioreactor and static system. Quantitative analysis of VE-cadherin expression by real-time RT-PCR (FIG. 8A) and FACS analysis of CD31 (FIG. 8B) and VE-cadherin (FIG. 8C) expression show no difference between stirred systems (i.e., Erlenmeyer and GBI spinner flask), RWV and static Petri dish groups.

Analysis and Discussion

In this study cultivation of human EBs under stirred conditions was investigated in order to establish a scalable technological platform for EB propagation while maintaining full differential potential.

Direct seeding of hESCs in stirred systems resulted in accelerated agglomeration, while EBs seeded into stirred systems after two days of culture in static conditions produced high cell and EB concentrations. Furthermore, direct seeding into the RWV bioreactor, which does not induce any shear forces on cells cultured therein, resulted in efficient EB formation.

Intensive mechanical cell-breaking or trypsinzation in order to create INF smaller than a few hundreds of cells resulted in a very small aggregates and a high concentration of single cells, leading to a low final EB concentration in the stirred systems.

In the present study three different stirring systems, characterized by induced shear forces and convection mass transfer mechanism, were compared to the RWV bioreactor and the static Petri dish systems which do not induce any shear forces and have mass transfer mechanism of diffusion. Propagation of hESCs for 10 cultivation days under mild shear forces in the shaking Erlenmeyer and the GBI spinner flask systems resulted in the formation of non agglomerated EBs exhibiting uniform morphology and size with a high yield of ~500 and ~200 EB/ml, respectively. EBs final concentration was 21-fold higher than in the RWV bioreactor and 2-fold higher than in the static Petri dish system.

Growth kinetics and cells viability were found higher for the EBs propagated in the GBI spinner flask and shaking Erlenmeyer compared to the PI spinner flask, consistent with lower apoptotic cells. These results demonstrate that cultivation in the GBI spinner flask results in a 5-fold increase of the final viable cell concentration compared to the RWV bioreactor, and 1.7-fold increase compared to the static system. Viability and the survival potential (measured by percentage of apoptotic cells) remained very high, while the LDH (lactate dehydrogenase) secretion was reduced and stabilized after removing the EBs to the GBI spinner flask. Furthermore, the growth curve of the cells in the GBI spinner flask had the fastest growth rate and constant logarithmic phase lacking lag phases, indicating stability of culture environment compared to the static Petri dish. However, cultivation in the PI spinner flask revealed poor results compared to the static Petri dish systems. In addition, cells grown in 55 ml RWV bioreactor demonstrated the slowest growth rate, lowest final cell concentration, and highest cell death and apoptotic cell percentage. Furthermore, EBs grown in static Petri dishes present accumulation of apoptotic cells in the center of the EBs. This is probably due to severe oxygen mass transfer limitation typical of diffusion mass transfer mechanism.

In the present study, human EBs propagated in the GBI spinner flask reached a maximum concentration of $5.0\times10^6$ viable cells/ml in eight days, with viability higher than 90%. No lag phase was observed in the GBI spinner flask system, while other systems presented different lag phases. This resulted in a 6.4 fold increase in cell expansion in 8 days, before the differentiation process became dominant.

The present study demonstrates that all three germ layers were presented during the cultivation period and in 10-day-old EBs. A clear decrease in the expression of Oct-4 and Rex-1, genes expressed in undifferentiated hESCs, was observed along with an increase in the expressions of endoderm, mesoderm and ectoderm genetic markers. The EBs grown in stirred systems demonstrate a high incidence of neural rosette formation, consistent with the increase in the NF68 and ND1 gene expressions. Rich capillary and well developed endothelial networks are also observed.

To evaluate the differentiation potential of EBs propagated in stirred systems, the present inventors chose to study the spontaneous cardiomyocytic and endothelial differentiation.

Previous studies of spontaneous cardiac differentiation of human EBs have reported a range of 8-10% [Kehat et al., 2001 (Supra)] and 25-70% of contracting EBs [Xu et al., 2002, (Supra)]. The results presented herein show clearly that cultivation in GBI spinner flasks has an advantage in differentiation towards contracting EBs. This is supported by higher expression of the cardiac specific α-MHC in EBs grown in the GBI spinner flask and the Erlenmeyer, and over 30% contracting EBs obtained after 10 days of cultivation. hESC-derived cardiomyocytes express cardiac-specific troponin I (cTnI), a subunit of the troponin complex that provides a calcium-sensitive molecular switch for the regulation of striated muscle contraction, which is detected only in the beating regions of the culture. Examination of the contracting EBs reveals certain cells carrying morphological and functional characteristics of cardiac muscle.

In summary, the present study discloses a robust protocol for human EB propagation and differentiation based on a stirred technological platform. The process established herein leads to increase in cell growth while maintaining the differentiation potential, compared to the standard static cultivation system and RWV bioreactor. In addition, the developed protocol leads to an improvement of existing differentiation methods.

Maintenance of suitable hydrodynamic conditions during hESCs seeding and cultivation was found to be crucial for the EB formation and propagation. The duration of EB formation in static Petri dishes and EB cultivation in stirred systems resulted in high EB yield, round homogenous shape and fastest growth rate.

The appearance of representative tissues derived from the three germ layers as well as primitive neuronal tube organization, blood vessel formation, and specific-endocrine secretion indicated that the initial developmental events were not altered in the stirred formed human EBs. Furthermore, well developed endothelial networks and contracting EBs with functional cardiac muscle cells were obtained after two weeks of cultivation. Collectively, this study defines the technological platform for controlled large-scale generation of hESC-derived cells for clinical and industrial applications, which can be implemented on an industrial controlled bioreactor.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

References

Additional References are Cited in Text

1. Cameron C M, Hu W S and Kaufman D S. (2006) Improved development of human embryonic stem cell-derived embryoid bodies by stirred vessel cultivation. Biotechnol Bioeng. August 5; 94(5):938-48;

2. Chisti Y. (2001) Hydrodynamic damage to animal cells. Crit. Rev Biotechnol. 21:67-110. Review;

3. Dang S M, Kyba M, Perlingeiro R, Daley G Q and Zandstra P W. (2002) Efficiency of embryoid body formation and hematopoietic development from embryonic stem cells in different culture systems. Biotechnol Bioeng. 78:442-53.

4. Dang S M, Gerecht-Nir S, Chen J, Itskovitz-Eldor J and Zandstra P W. (2004) Controlled, scalable embryonic stem cell differentiation culture. Stem Cells. 22:275-82;

5. Gerecht-Nir, S., Cohen S, Itskovitz-Eldor, J, (2004). Bioreactor Cultivation Enhances the Efficiency of Human Embryoid Body (hEB) Formation and Differentiation. Biotechnol Bioeng. 2004 Jun. 5; 86(5):493-502;

6. Kehat I, Kenyagin-Karsenti D, Snir M, Segev H, Amit M, Gepstein A, Livne E, Binah O, Itskovitz-Eldor J and Gepstein L. (2001) Human embryonic stem cells can differentiate into myocytes with structural and functional properties of cardiomyocytes;

7. Livak K. J. and Schmittgen T. D. (2001) Analysis of relative gene expression data using real-time quantitative PCR and the 2(-Delta Delta C(T)) Method. Methods. December; 25(4):402-8;

8. Schroeder M, Niebruegge S, Werner A, Willbold E, Burg M, Ruediger M, Field L J, Lehmann J and Zweigerdt R. (2005) Differentiation and lineage selection of mouse embryonic stem cells in a stirred bench scale bioreactor with automated process control. Biotechnol Bioeng. December 30; 92(7):920-33;

9. Wartenberg M, Gunther J, Hescheler J and Sauer H. (1998) The embryoid body as a novel in vitro assay system for antiangiogenic agents. Lab Invest. October; 78(10):1301-14;

10. Xu C, Police S, Rao N and Carpenter M K. (2002) Characterization and enrichment of cardiomyocytes derived from human embryonic stem cells. Circ Res. September 20; 91(6):501-8;

11. Zandstra P W, Bauwens C, Yin T, Liu Q, Schiller H, Zweigerdt R, Pasumarthi K B and Field U. (2003) Scalable production of embryonic stem cell-derived cardiomyocytes. Tissue Eng. August; 9(4):767-78. Erratum in: Tissue Eng. 2003 December; 9(6)1331;

12. Zweigerdt R, Burg M, Willbold E, Abts H and Ruediger M. (2003) Generation of confluent cardiomyocyte monolayers derived from embryonic stem cells in suspension: a cell source for new therapies and screening strategies. Cytotherapy. 5(5):399-413;

13. PCT Publication WO 04039966;

14. U.S. Pat. Appl. No. 20060148078;

15. U.S. Pat. Appl. No. 20040096967;

16. U.S. Pat. Appl. No. 20060134782;

What is claimed is:

1. A method of generating human embryoid bodies comprising:
   (a) dispersing into a culture medium human embryonic stem cell colonies into initiation nucleus foci (INF)
   (b) culturing said human embryonic stem cells resultant of step (a) at an initial concentration range of at least $0.5 \times 10^6 +/- 10\%$ cells/ml for $2+/-10\%$ days under static conditions; and subsequently
   (c) culturing said cells resultant of step (b) under dynamic conditions using a Glass Bulb-shaped Impeller (GBI), wherein a growth rate of said cells is at least 1.6 times/day during 6 days of said dynamic conditions,
   thereby generating the human embryoid bodies at $200+/-10\%$ embryoid bodies per milliliter of culture media from said human embryonic stem cells.

2. The method of claim 1, wherein said dispersing is effected detaching said colonies from a support thereof using type IV Collagenase.

3. The method of claim 1, wherein said static conditions comprise culturing said embryonic stem cells in a Rotating Wall Vessel (RWV) bioreactor.

4. The method of claim 1, wherein said dynamic conditions enable generation of embryoid bodies which include no more than 4% of apoptotic cells following 10 days in culture.

5. The method of claim 1, wherein said embryoid bodies are devoid of necrotic centers.

6. The method of claim 1, wherein an average diameter of said embryoid bodies generated following 10 days in culture does not exceed about 400 μm.

7. The method of claim 1, wherein said dynamic conditions comprise stirring said GBI at a rate of 75 ±10% revolutions per minute (RPM).

8. The method of claim 1, wherein cells comprised in said embryoid bodies exhibit normal karyotype.

9. The method of claim 1, wherein said culturing of said embryonic stem cells is effected in a culture medium selected suitable for embryoid bodies formation.

10. The method of claim 9, wherein said culture medium comprises 80% KO-DMEM, 20% serum, 1% Penicillin-Streptomycin, 1 mM L-glutamine, and 1% non-essential amino acid stock.

11. The method of claim 1, wherein said embryoid bodies differentiate into cardiomyocytes.

12. The method of claim 1, wherein said embryoid bodies spontaneously contract when transferred to gelatin-coated plates.

13. The method of claim 1, wherein when said culturing under said dynamic conditions is effected for about 6 days then said culture comprises at least $3.7 \times 10^6 \pm 10\%$ viable cells/ml.

14. The method of claim 1, wherein said growth rate of said cells is at least 2.3 times/day during 6 days of said dynamic conditions.

15. The method of claim 1, wherein each of said initiation nucleus foci comprises about 1300-1600 of said embryonic stem cells.

* * * * *